United States Patent
Shabat et al.

(10) Patent No.: US 10,420,845 B2
(45) Date of Patent: Sep. 24, 2019

(54) TAGGABLE HETEROAROMATIC DRUGS AND CONJUGATES THEREOF

(71) Applicant: Ramot at Tel-Aviv University Ltd., Tel Aviv (IL)

(72) Inventors: Doron Shabat, Tel Aviv (IL); Ronit Satchi-Fainaro, Tel Aviv (IL); Samer Gnaim, Baqa El-Garbia (IL); Anna Scomparin, Tel Aviv (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 15/737,247

(22) PCT Filed: Jun. 16, 2016

(86) PCT No.: PCT/IL2016/050639
§ 371 (c)(1),
(2) Date: Dec. 15, 2017

(87) PCT Pub. No.: WO2016/203478
PCT Pub. Date: Dec. 22, 2016

(65) Prior Publication Data
US 2018/0169252 A1    Jun. 21, 2018

Related U.S. Application Data

(60) Provisional application No. 62/181,277, filed on Jun. 18, 2015.

(51) Int. Cl.
| | |
|---|---|
| *C07D 491/22* | (2006.01) |
| *A61K 47/54* | (2017.01) |
| *A61K 31/436* | (2006.01) |
| *A61K 31/4188* | (2006.01) |
| *A61K 31/497* | (2006.01) |
| *A61K 31/519* | (2006.01) |
| *C07D 487/04* | (2006.01) |
| *C07D 215/44* | (2006.01) |
| *A61P 35/00* | (2006.01) |
| *A61K 31/4184* | (2006.01) |
| *A61K 31/4745* | (2006.01) |
| *A61K 31/496* | (2006.01) |
| *A61K 31/513* | (2006.01) |

(52) U.S. Cl.
CPC ........ *A61K 47/555* (2017.08); *A61K 31/4184* (2013.01); *A61K 31/4188* (2013.01); *A61K 31/436* (2013.01); *A61K 31/4745* (2013.01); *A61K 31/496* (2013.01); *A61K 31/497* (2013.01); *A61K 31/513* (2013.01); *A61K 31/519* (2013.01); *A61K 47/54* (2017.08); *A61P 35/00* (2018.01); *C07D 215/44* (2013.01); *C07D 487/04* (2013.01); *C07D 491/22* (2013.01)

(58) Field of Classification Search
CPC .. C07D 491/22; C07D 487/04; C07D 401/12; A61K 47/48; A61K 31/497; A61K 31/519; A61K 31/4188; A61K 31/436; A61P 35/00
See application file for complete search history.

(56) References Cited

U.S. PATENT DOCUMENTS

2006/0233794 A1    10/2006    Law et al.

FOREIGN PATENT DOCUMENTS

| CN | 104230845 | 12/2014 |
|---|---|---|
| WO | WO 2005/111063 | 11/2005 |

OTHER PUBLICATIONS

Schulz, Molecular Biology of Human Cancers: Chapter 1, Springer, pp. 1-23 (2007).*
Simone, Oncology: Introduction, Cecil Textbook of Medicine, 20th Edition, vol. 1, pp. 1004-1101 O, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Gnaim et al., "Tagging the Untaggable: a Difluoroalkyl-Sulfinate Ketone-Based Reagent for Direct C-H Functionalization of Bioactive Heteroarenes", Bioconjugate Chem. 27(9):1965-1971; 2016.
International Search Report issued in application No. PCT/IL2016/050639 dated Sep. 25, 2016.
Written Opinion issued in International Application No. PCT/IL2016/050639 dated Sep. 25, 2016.
Zhou et al., "Bioconjugation by Native Chemical Tagging of C—H Bonds", Journal of the American Chemical Society., vol. 134, pp. 12994-12997. (2014).
Abstract of Pinhassi et al.,"Arabinogalactan-Folic Acid-Drug Conjugate for Targeted Delivery and Target-Activated Release of Anticancer Drugs to Folate Receptor-Overexpressing Cells" Biomacromolecules, 2010, 11(1), 294-303.

* cited by examiner

*Primary Examiner* — Deepak R Rao
(74) *Attorney, Agent, or Firm* — Knobbe, Martens, Olson & Bear, LLP

(57) ABSTRACT

The present disclosure provides heteroarene-based drug derivatives having a "clickable" ketone group, as well as conjugates of said drug derivatives with targeting moieties capable of binding to extracellular antigens; and pharmaceutical compositions comprising them.

25 Claims, 7 Drawing Sheets

TAGGABLE HETEROAROMATIC DRUGS AND CONJUGATES THEREOF

CROSS REFERENCE TO RELATED APPLICATIONS

This application is the U.S. National Phase under 35 U.S.C. § 371 of International Application No. PCT/IL2016/050639 filed Jun. 16, 2016, designating the U.S., and published as WO 2016/203478 on Dec. 22, 2016 which claims the benefit of U.S. Provisional Application No. 62/181,277 filed Jun. 18, 2015. Any and all applications for which a foreign or domestic priority claim is identified above and/or in the Application Data Sheet as filed with the present application are hereby incorporated by reference under 37 CFR 1.57.

TECHNICAL FIELD

The present invention provides heteroarene-based drug derivatives having a "clickable" ketone group, as well as conjugates of said drug derivatives with targeting moieties capable of binding to extracellular antigens and pharmaceutical compositions thereof.

Abbreviations: ACN, acetonitrile; AcOH, acetic acid; $Ac_2O$, acetic anhydride; $CHCl_3$, chloroform; CPT, camptothecin; DBTL, dibutyltin dilaurate; DCM, dichloromethane; DMAP, dimethylaminopyridine; DMF, dimethylformamide; DMSO, dimethylsulfoxide; $Et_2O$, diethyl ether; EtOAc, ethylacetate; EtOH, ethanol; FBS, fetal bovine serum; FR, folate receptor; Hex, n-hexane; HBTU, (2-(1H-benzotriazol-1-yl)-1,1,3,3-tetramethyluronium hexafluorophosphate); HMPA, hexamethylphosphoramide [?]; HMTA, hexamethylenetetra amine; HPLC, high pressure liquid chromatography; LHMDS, lithium hexamethyldisilazide; MeOH, methanol; MTX, methotrexate; PBS, phosphate buffered saline; PEG, polyethylene glycol; PTSA, p-toluenesulfonic acid; RPMI, Roswell Park Memorial Institute; TBHP, tertbutylhydroperoxide; TFA, trifluoroacetic acid; THF, tetrahidrofuran; TLC, thin layer chromatography; TMZ, temozolomide; TsOH, p-toluenesulfonic acid.

BACKGROUND ART

Bioconjugation is an essential tool in chemical biology for attaining controlled release of a small molecule with medicinal activity. It is typically implemented through chemoselective modification of native functional groups present on the target molecule (Zhou et al., 2013a). For example, amines can be chemoselectively derivatized through amide linkages, azides or acetylenes through the "click" reaction (Kolb et al., 2001) and carbonyl groups through the oxime ligation (Ulrich et al., 2014). Although many medicinal agents contain traditional "taggable" functional groups, some compounds present the challenge of not having any apparent chemical handles. As a further layer of complexity, some molecules require an orthogonal handle for bioconjugation.

A general C—H functionalization method for the tagging of heteroarenes, more particularly heteroarene-based drugs, has been recently been introduced by the group of Baran (Gui et al., 2014; Zhou et al., 2013b; Fujiwara et al., 2012; Bruckl et al., 2012; Ji et al., 2011). According to that method, an azide-containing sulfinate reagent, more specifically sodium (difluoroalkylazido)sulfinate, allows the appendage of azidoalkyl chain onto a heteroaromatic, and the synthesized azide-linked drug is then attached to a monoclonal antibody, via a succinimide-containing linker, by reacting with a dibenzoazocan-4-yne (referred to in the publication as dibenzylazacyclooctyne)-containing monoclonal antibody in a copper-free azide-alkyne cycloaddition, so as to obtain a drug-antibody conjugate.

SUMMARY OF INVENTION

The present invention relates to a new chemical linker strategy for construction of photo-labile or acid-sensitive conjugates, e.g., folate conjugates, of heteroarene-based drugs or bioactive reagents including those that a priori have neither limited or no tagging option, and demonstrates the efficacy and chemical properties of such conjugates. The main advantage of this methodology is the ability to introduce a "clickable" ketone group into the heteroarene-based drug molecule while preserving its biological activity. Upon hydrolysis under slightly acidic conditions, i.e., physiological conditions, the drug conjugate releases the functionalized drug in a wide-ranging release rates.

In one aspect, the present invention provides a compound of the formula I:

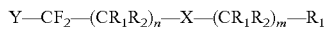

$$Y—CF_2—(CR_1R_2)_n—X—(CR_1R_2)_m—R_1 \qquad I$$

wherein

Y is a drug or a bioactive reagent, comprising a heteroaromatic ring and linked via a carbon atom of said heteroaromatic ring;

X is carbonyl, or cyclic ketal substituted with 1 to 4 groups each independently is phenyl or naphtyl substituted ortho to the carbon of attachment with —$NO_2$, and optionally further substituted at any position other than ortho to the carbon of attachment with one or more groups each independently selected from —O—($C_1$-$C_8$), —($C_1$-$C_8$)alkyl, —N(R')$_2$, or halogen, wherein R' each independently is —($C_1$-$C_8$)alkyl or H;

$R_1$ and $R_2$ each independently is H, halogen, —$OR_3$, —CO—$R_3$, —CO—$OR_3$, —OCO—$OR_3$, —OCO—N($R_3$)$_2$, —CN, —$NO_2$, —$SR_3$, —N($R_3$)$_2$, —CO—N($R_3$)$_2$, —($C_1$-$C_8$)alkyl, —($C_2$-$C_8$)alkenyl, —($C_2$-$C_8$)alkynyl, ($C_3$-$C_{10}$)cycloalkyl, ($C_6$-$C_{14}$)aryl, or 4-12-membered heterocyclyl;

$R_3$ is H, —($C_1$-$C_{18}$)alkyl, —($C_2$-$C_{18}$)alkenyl, or —($C_2$-$C_{18}$)alkynyl; and n and m each independently is an integer of 1-8, or a pharmaceutically acceptable salt thereof.

In another aspect, the present invention provides a conjugate of the formula II:

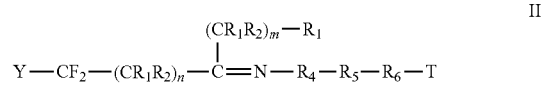

$$Y—CF_2—(CR_1R_2)_n—\underset{\underset{R_1}{\overset{(CR_1R_2)_m—R_1}{|}}}{C}=N—R_4—R_5—R_6—T \qquad II$$

wherein

Y is a drug or a bioactive reagent, comprising a heteroaromatic ring and linked via a carbon atom of said heteroarimatic ring;

$R_1$ and $R_2$ each independently is H, halogen, —$OR_3$, —CO—$R_3$, —CO—$OR_3$, —OCO—$OR_3$, —OCO—N($R_3$)$_2$, —CN, —$NO_2$, —$SR_3$, —N($R_3$)$_2$, —CO—N($R_3$)$_2$, —($C_1$-$C_8$)alkyl, —($C_2$-$C_8$)alkenyl, —($C_2$-$C_8$)alkynyl, ($C_3$-$C_{10}$)cycloalkyl, ($C_6$-$C_{14}$)aryl, or 4-12-membered heterocyclyl;

$R_3$ is H, —($C_1$-$C_{18}$)alkyl, —($C_2$-$C_{18}$)alkenyl, or —($C_2$-$C_{18}$)alkynyl;

$R_4$ is absent, or is selected from —NH—($CH_2$)$_p$—, —NH—CO—($CH_2$)$_p$—, —NH—CO—NH—($CH_2$)$_p$—, —NH—CO—, —O—(CH$_2$)$_p$—, —O—(CH$_2$)$_p$—, —O—CO—(CH$_2$)$_p$—, —O—CO—NH—(CH$_2$)$_p$—, or —O—CO—O—(CH$_2$)$_p$—;

R$_5$ is a polymer-, protein-, peptide-, or carbohydrate moiety;

R$_6$ is H, —(CH$_2$)$_y$—OH, —(CH$_2$)$_y$—SH, —(CH$_2$)$_y$—NH$_2$, —(CH$_2$)$_y$—COOH, —(CH$_2$)$_y$—SO$_3$H, or a divalent radical selected from —(CH$_2$)$_y$—O—, —(CH$_2$)$_y$—S—, —(CH$_2$)$_y$—NH—, —(CH$_2$)$_y$—COO— or —(CH$_2$)$_y$—SO$_3$—;

n and m each independently is an integer of 1-8;

p and y each independently is an integer of 0-8; and

T is absent, or is a targeting moiety capable of binding to an extracellular antigen and linked via a functional group thereof, provided that when T is absent R$_6$ is not a divalent radical, and when T is a targeting moiety R$_6$ is a divalent radical, or a pharmaceutically acceptable salt thereof.

In one particular such aspect, the present invention provides a conjugate of the formula II wherein R$_6$ is H, —(CH$_2$)$_y$—OH, —(CH$_2$)$_y$—SH, —(CH$_2$)—NH$_2$, —(CH$_2$)$_y$—COOH, or —(CH$_2$)$_y$—SO$_3$H, wherein y is an integer of 0-8, and T is absent; and in another particular such aspect, the present invention provides a conjugate of the formula II wherein R$_6$ is a divalent radical, and T is a targeting moiety capable of binding to an extracellular antigen.

In a further aspect, the present invention provides a pharmaceutical composition comprising either a compound of the formula I as defined above wherein X is not carbonyl; or a conjugate of the formula II as defined above, or a pharmaceutically acceptable salt thereof, herein also referred to as the active agent, and a pharmaceutically acceptable carrier.

The active agent as referred to herein can be used for prevention, treatment of management of various diseases, disorders or indications treatable by administration of the drug or a bioactive reagent Y composing said compound or conjugate.

In yet another aspect, the present invention thus relates, e.g., to a method for treatment of a cancer in an individual in need thereof, comprising administering to said individual a therapeutically effective amount of a conjugate of the formula IT as defined above, or a pharmaceutically acceptable salt thereof, wherein Y is an anticancer drug or an antineoplastic drug, and said targeting moiety is capable of binding to an extracellular antigen present on the cells of said cancer.

In still another aspect, the present invention relates to a conjugate of the formula II as defined above, or a pharmaceutically acceptable salt thereof, wherein Y is an anticancer drug or an antineoplastic drug, and said targeting moiety is capable of binding to an extracellular antigen present on the cells of said cancer, for use in the treatment of cancer.

DETAILED DESCRIPTION

According to the C—H functionalization method developed by the group of Baran and discussed above, an azide-containing sulfinate reagent allows the addition of azidoalkyl chain onto a heteroarene-based drug, and the azide-linked drug synthesized is then attached to a monoclonal antibody, via a linker, by reacting with a dibenzoazocan-4-yne-containing monoclonal antibody in a copper-free azide-alkyne cycloaddition, so as to obtain a drug-antibody conjugate. Baran does not show the hydrolysis of the drug conjugate obtained as a function of pH and incubation time; however, it may be postulated that upon hydrolysis under physiological conditions, either the drug-difluoroalkylene-azide or the drug-difluoroalkylene-8,9-dihydro-1H-dibenzo [b,f][1,2,3]triazolo[4,5-d]azocine is released. As currently known, such an azide-linked drug loses most. i.e., up to 99%, of its biological activity compared with the underivatized (native) drug.

It has now been found, in accordance with the present invention, that heteroarene-based drugs, i.e., drugs comprising a heteroaromatic ring, which lack an appropriate functional group for linker chemistry, can be functionalized using an alkylating sulfinate reagent bearing a protected ketone functional group, recently developed by the present inventors, more particularly sodium 1,1-difluoro-4-(2-methyl-1,3-dioxolan-2-yl)butane-1-sulfinate via a one-step synthesis. As surprisingly found, a heteroarene-based drug derivative prepared using said alkylating sulfinate reagent preserves the biological activity of the underivatized drug.

The introduction of a "clickable" ketone group into the heteroarene-based drug molecule allows for the bioconjugation of the drug molecule via an acid labile hydrazone linkage or through a photo-labile ketal, for controlled-release applications. When a stable linkage is required, the oxime ligation could also be used to link between the ketone-tagged moiety and an amine-oxy derivative. Indeed, as further shown herein, drug derivatives as described above can be bioconjugated through a linker such as polyethylene glycol (PEG) or a pseudoPEG, having suitable functional groups, to a targeting moiety capable of binding to an extracellular antigen, e.g., an antibody, sugar, lectin, hormone, peptidomimetic, or folic acid as exemplified herein, as schematically illustrated in Scheme 1.

Figure 1:
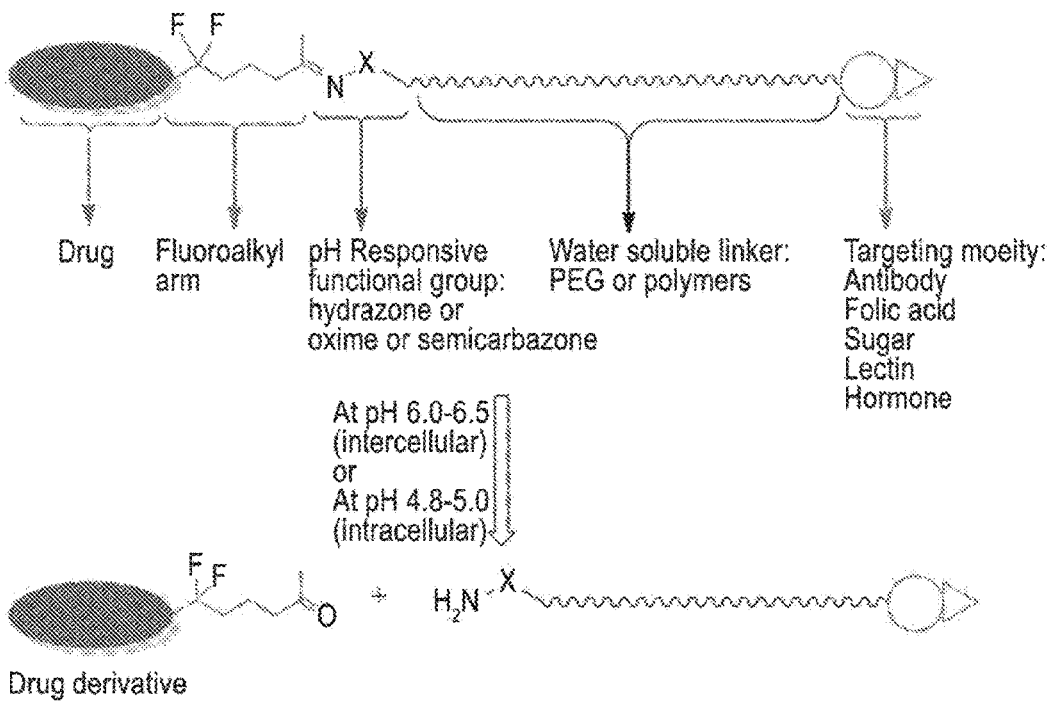
FIG. 1 illustrates schematically the bioconjugation approach disclosed herein, as well as the bioconjugate hydrolysis releasing the drug-derivative.

Upon hydrolysis under slightly acidic (pH 4.8-6.0) conditions that might mimic endosomal and liposomal environments, the drug conjugate releases the functionalized drug in a wide-ranging release rates. The bioconjugation approach disclosed herein, as well as the bioconjugate hydrolysis releasing the drug-derivative, is schematically illustrated in FIG. 1.

In one aspect, the present invention thus provides a compound, also referred to herein as "drug derivative", of the formula I:

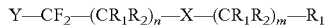

I wherein

Y is a drug or a bioactive reagent, comprising a heteroaromatic ring and linked via a carbon atom of said heteroaromatic ring;

X is carbonyl, or cyclic ketal substituted with 1 to 4 groups each independently is phenyl or naphtyl substituted ortho to the carbon of attachment with —$NO_2$, and optionally further substituted at any position other than ortho to the carbon of attachment with one or more groups each independently selected from —O—($C_1$-$C_8$), —($C_1$-$C_8$)alkyl, —$N(R')_2$, or halogen, wherein R' each independently is —($C_1$-$C_8$)alkyl or H;

$R_1$ and $R_2$ each independently is H, halogen, —$OR_3$, —CO—$R_3$, —CO—$OR_3$, —OCO—$OR_3$, —OCO—$N(R_)_2$, —CN, —$NO_2$, —$SR_3$, —$N(R_3)_2$, —CO—$N(R_3)_2$, —($C_1$-$C_8$)alkyl, —($C_2$-$C_8$) alkenyl, —($C_2$-$C_8$)alkynyl, ($C_3$-$C_{10}$)cycloalkyl, ($C_6$-$C_{14}$)aryl, or 4-12-membered heterocyclyl;

$R_3$ is H, —($C_1$-$C_{18}$)alkyl, —($C_2$-$C_{18}$)alkenyl, or —($C_2$-$C_{18}$)alkynyl; and n and m each independently is an integer of 1-8, or a pharmaceutically acceptable salt thereof.

The term "halogen" as used herein refers to a halogen and includes fluoro, chloro, bromo, and iodo, and it is preferably fluoro or chloro.

The term "alkyl" as used herein typically means a linear or branched saturated hydrocarbon radical having 1-18 carbon atoms and includes, e.g., methyl, ethyl, n-propyl, isopropyl, n-butyl, sec-butyl, isobutyl, tert-butyl, n-pentyl, isoamyl, 2,2-dimethylpropyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and the like. Preferred are ($C_1$-$C_8$)alkyl groups, more preferably ($C_1$-$C_4$)alkyl groups, most preferably methyl, ethyl or propyl. The terms "alkenyl" and "alkynyl" typically mean linear and branched hydrocarbon radicals having 2-18 carbon atoms and 1 double or triple bond, respectively, and include ethenyl, propenyl, 3-butenyl, 2-ethenylbutyl, 1- and 2-pentenyl, 1-, 2- and 3-hexenyl, 1-, 2-, 3- and 4-heptenyl, 1-, 2-, 3- and 4-octenyl, 1-, 2-, 3- and 4-nonenyl, 1-, 2-, 3-, 4- and 5-decenyl, and the like, and propynyl, 2-butynyl, 1- and 2-pentynyl, 1-, 2- and 3-hexynyl, 1-, 2-, 3- and 4-heptynyl, 1-, 2-, 3- and 4-octynyl, 1-, 2-, 3- and 4-nonynyl, 1-, 2-, 3-, 4- and 5-decynyl, and the like, $C_2$-$C_6$ alkenyl and alkynyl radicals are preferred, more preferably $C_2$-$C_4$ alkenyl and $C_2$-$C_4$ alkynyl. The alkyl, alkenyl and alkynyl defined herein may optionally be substituted with one or more groups each independently selected from —OR', —COR', —COOR', —OCOOR', —OCON(R')$_2$, —CN, —$NO_2$, —SR', —($C_1$-$C_8$)alkyl, —$N(R')_2$, —CON(R')$_2$, —$SO_2R'$, —$SO_2NHR'$, or —S(=O)R', wherein R' is H or unsubstituted ($C_1$-$C_8$)alkyl.

The term "alkylene" as used herein means typically means a divalent straight or branched hydrocarbon radical having 1-8 carbon atoms and includes, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, octylene and the like. Preferred are ($C_3$-$C_8$)alkylene, more preferably ($C_3$-$C_6$)alkylene.

The term "cycloalkyl" as used herein means a cyclic or bicyclic hydrocarbyl group having 3-10 carbon atoms such as cyclopropyl, cyclobutyl, cyclopentyl, cyclohexyl, cycloheptyl, cyclooctyl, adamantyl, bicyclo[3.2.1]octyl, bicyclo [2.2.1]heptyl, and the like. Preferred are ($C_5$-$C_{10}$)cycloalkyls, more preferably ($C_5$-$C_7$)cycloalkyls. The cycloalkyl defined herein may optionally be substituted with one or more groups each independently selected from —OR', —COR', —COOR', —OCOOR', —OCON(R')$_2$, —CN, —$NO_2$, —SR', —($C_1$-$C_8$)alkyl, —$N(R')_2$, —CON (R')$_2$, —$SO_2R'$, —$SO_2NHR'$, or —S(=O)R', wherein R' is H or unsubstituted ($C_1$-$C_8$)alkyl.

The term "aryl" denotes an aromatic carbocyclic group having 6-14 carbon atoms consisting of a single ring or multiple rings either condensed or linked by a covalent bond such as, but not limited to, phenyl, naphthyl, phenanthryl, and biphenyl. The aryl defined herein may optionally be substituted with one or more groups each independently selected from —OR', —COR', —COOR', —OCOOR', —OCON(R')$_2$, —CN, —$NO_2$, —SR', —($C_1$-$C_8$)alkyl, —$N(R')_2$, —CON(R')$_2$, —$SO_2R'$, —$SO_2NHR'$, or —S(=O) R', wherein R' is H or unsubstituted ($C_1$-$C_8$)alkyl.

The term "heterocyclic ring" denotes a mono- or polycyclic non-aromatic ring of 4-12 atoms containing at least one carbon atom and one to three heteroatoms selected from sulfur, oxygen or nitrogen, which may be saturated or unsaturated, i.e., containing at least one unsaturated bond. Preferred are 5- or 6-membered heterocyclic rings. The term "heterocyclyl" as used herein refers to any univalent radical derived from a heterocyclic ring as defined herein by removal of hydrogen from any ring atom. Examples of such radicals include, without limitation, piperidino, 4-morpholinyl, or pyrrolidinyl. The heterocyclyl defined herein may optionally be substituted, at any position of the ring, with one or more groups each independently selected from —OR', —COR', —COOR', —OCOOR', —OCON(R')$_2$, —CN, —$NO_2$, —SR', —($C_1$-$C_8$)alkyl, —$N(R')_2$, —CON (R')$_2$, —$SO_2R'$, —$SO_2NHR'$, or —S(=O)R', wherein R' is H or unsubstituted ($C_1$-$C_8$)alkyl.

In certain embodiments, the present invention provides a compound of the formula I, wherein $R_1$ and $R_2$ each independently is H, halogen, —$OR_3$, —CO—$R_3$, —CO—$OR_3$, —OCO—$OR_3$, —OCO— $N(R_3)_2$, —CN, —$NO_2$, —$SR_3$, —$N(R_3)_2$, —CO—$N(R_3)_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl, wherein $R_3$ is H, —($C_1$-$C_4$)alkyl, —($C_2$-$C_4$)alkenyl, or —($C_2$-$C_4$)alkynyl. Preferred such embodiments are those wherein $R_3$ is H, methyl, ethyl or propyl, more preferably H.

In certain embodiments, the present invention provides a compound of the formula I, wherein n is 3, 4 or 5, preferably 3; or m is 1, 2 or 3, preferably 1.

In certain embodiments, the present invention provides a compound of the formula I, wherein $R_1$ and $R_2$ each independently is H, halogen, —$OR_3$, —CO—$R_3$, —CO—$OR_3$, —OCO—$OR_3$, —OCO—$N(R_3)_2$, —CN, —$NO_2$, —$SR_3$, —$N(R_3)_2$, —CO—$N(R_3)_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl, wherein $R_3$ is H, —($C_1$-$C_4$)alkyl, —($C_2$-$C_4$)alkenyl, or —($C_2$-$C_4$)alkynyl, preferably H, methyl, ethyl or propyl; n is 3, 4 or 5, preferably 3; and m is 1, 2 or 3, preferably 1. Particular such embodiments are those wherein $R_1$ and $R_2$ each independently is H, halogen, —OH, —COH, —COOH, —OCOOH, —OCO—$NH_2$, —CN, —$NO_2$, —SH, —$NH_2$, —CO—$NH_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl; n is 3; and m is 1. In more particular such embodiments, $R_1$ and $R_2$ are H.

In certain embodiments, the present invention provides a compound of the formula I, wherein the drug or bioactive reagent Y is selected from anticancer drugs, antineoplastic drugs, antifungal drugs, antibacterial drugs, antiviral drugs, cardiac drugs, neurological drugs, psychoactive drugs such as caffeine, drugs of abuse, i.e., drugs taken for nonmedicinal reasons (usually for mind-altering effects), alkaloids, antibiotics, bioactive peptides, steroids, steroid hormones, peptide (e.g., polypeptide) hormones, interferons, interleukins, narcotics, nucleic acids, pesticides, or prostaglandins.

In particular such embodiments, the drug or bioactive reagent Y is an anticancer drug such as a chemotherapeutic drug, e.g., camptothecin or a derivative thereof such as 10-hydroxycamptothecin or any other camptothecin substituted at the 7-, 9- or 10-position (as described in Basil and Moro, *Expert Opin Ther Pat.*, 2009, 19(5), 555-574), bosutinib, or methotrexate formerly known as amethopterin; or an antineoplastic drug such as an alkylating antineoplastic agent, e.g., temozolomide, uramustine or bendamustine.

In certain embodiments, the present invention provides a compound of the formula I as defined in any one of the embodiments above, wherein X is carbonyl, i.e., a compound of the formula Ia:

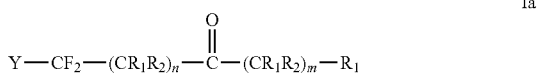

Ia

Particular compounds of the formula Ia are those wherein $R_1$ and $R_2$ each independently is H, halogen, —OH, —COH, —COOH, —OCOOH, —OCO—$NH_2$, —CN, —$NO_2$, —SH, —$NH_2$, —CO—$NH_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl, preferably H; n is 3; and m is 1. Specific such compounds exemplified herein are those wherein $R_1$ and $R_2$ are H; n is 3; m is 1; and the drug moiety Y is CPT, TMZ, bosutinib or MTX, herein identified compounds 2a, 3a, 4a, and 5a, respectively.

In certain embodiments, the present invention provides a compound of the formula I as defined in any one of the embodiments above, wherein X is cyclic ketal substituted as defined above, i.e., a compound of the formula Ib. As shown herein, such compounds are, in fact, prodrugs for the corresponding compounds wherein X is carbonyl, and are converted to said corresponding compounds upon exposure to an irradiation, e.g., UV irradiation as exemplified herein, or a visible or near infra-red irradiation.

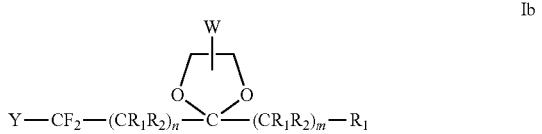

Ib

W = 1-4 groups each being phenyl or naphtyl substituted as defined above

In particular such embodiments, X is cyclic ketal substituted with 1 or 2 groups each independently is phenyl substituted ortho to the carbon of attachment with —$NO_2$, —CN, or —COO—($C_1$-$C_4$)alkyl, preferably —$NO_2$, and optionally further substituted at any position other than ortho to the carbon of attachment with one or more groups each independently selected from —O—($C_1$-$C_4$), preferably —O—($C_1$-$C_2$), more preferably —$OCH_3$. In more particular such embodiments, X is cyclic ketal substituted with 4,5-dimethoxy,2-nitrophenyl group, or cyclic ketal substituted with two 4,5-dimethoxy,2-nitrophenyl groups wherein each one of said groups is linked to a different carbon atom of the ketal.

Particular such compounds are those wherein X is cyclic ketal substituted with 4,5-dimethoxy,2-nitrophenyl group; $R_1$ and $R_2$ each independently is H, halogen, —OH, —COH, —COOH, —OCOOH, —OCO—$NH_2$, —CN, —$NO_2$, —SH, —$NH_2$, —CO—$NH_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl, preferably H; n is 3; and m is 1. Specific such compounds are those wherein $R_1$ and $R_2$ are H; n is 3; m is 1; and the drug moiety Y is CPT (herein identified compound 6), TMZ, bosutinib, or MTX.

The drug derivatives of the formula I wherein X is carbonyl may be synthesized according to any technology or procedure known in the art, e.g., via a one-step synthesis using the alkylating sulfinate reagent sodium 1,1-difluoro-4-(2-methyl-1,3-dioxolan-2-yl)butane-1-sulfinate, as described in the Examples section hereinafter with respect to, e.g., CPT, TMZ, bosutinib and MTX. Conversion of these drug derivatives to their corresponding prodrugs, wherein X is cyclic ketal substituted as defined above, can be carried out, e.g., by reacting said drug derivatives with ethylene glycol substituted at one or both of its carbon atoms with, e.g., 4,5-dimethoxy,2-nitrophenyl group, as described in the Examples section with respect to such a CPT prodrug herein identified compound 6.

In another aspect, the present invention provides a conjugate of the formula II:

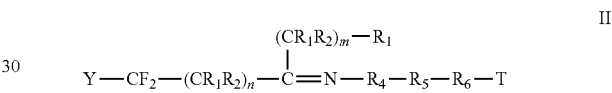

II wherein

Y is a drug or a bioactive reagent, comprising a heteroaromatic ring and linked via a carbon atom of said heteroarimatic ring;

$R_1$ and $R_2$ each independently is H, halogen, —$OR_3$, —CO—$R_3$, —CO—$OR_3$, —OCO—$OR_3$, —OCO—$N(R_3)_2$, —CN, —$NO_2$, —$SR_3$, —$N(R_3)_2$, —CO—$N(R_3)_2$, —($C_1$-$C_8$)alkyl, —($C_2$-$C_8$)alkenyl, —($C_2$-$C_8$)alkynyl, ($C_3$-$C_{10}$)cycloalkyl, ($C_6$-$C_{14}$)aryl, or 4-12-membered heterocyclyl;

$R_3$ is H, —($C_1$-$C_{18}$)alkyl, —($C_2$-$C_{18}$)alkenyl, or —($C_2$-$C_{18}$)alkynyl;

$R_4$ is absent, or is selected from —NH—($CH_2$)$_p$—, —NH—CO—($CH_2$)$_p$—, —NH—CO—NH—($CH_2$)$_p$—, —NH—CO—O—($CH_2$)$_p$—, —O—($CH_2$)$_p$—, —O—CO—($CH_2$)$_p$—, —O—CO—NH—($CH_2$)$_p$—, or —O—CO—O—($CH_2$)$_p$—;

$R_5$ is a polymer-, protein-, peptide-, or carbohydrate moiety;

$R_6$ is H, —($CH_2$)$_y$—OH, —($CH_2$)$_y$—SH, —($CH_2$)$_y$—$NH_2$, —($CH_2$)$_y$—COOH, —($CH_2$)$_y$—$SO_3H$, or a divalent radical selected from —($CH_2$)$_y$—O—, —($CH_2$)$_y$—S—, —($CH_2$)—NH—, —($CH_2$)$_y$—COO— or —($CH_2$)$_y$—$SO_3$—;

n and m each independently is an integer of 1-8;

p and y each independently is an integer of 0-8; and

T is absent, or is a targeting moiety capable of binding to an extracellular antigen and linked via a functional group thereof, provided that when T is absent $R_6$ is not a divalent radical, and when T is a targeting moiety $R_6$ is a divalent radical, or a pharmaceutically acceptable salt thereof.

In certain embodiments, the present invention provides a conjugate of the formula II, wherein $R_1$ and $R_2$ each independently is H, halogen, —$OR_3$, —CO—$R_3$, —CO—$OR_3$, —OCO—OR$_3$, —OCO—N(R$_3$)$_2$, —CN, —NO$_2$, —SR$_3$, —N(R$_3$)$_2$, —CO—N(R$_3$)$_2$, —(C$_1$-C$_4$)alkyl, —(C$_2$-C$_4$)alkenyl, —(C$_2$-C$_4$)alkynyl, (C$_3$-C$_{10}$))cycloalkyl, (C$_6$-C$_{14}$)aryl, or 4-12-membered heterocyclyl, wherein R$_3$ is H, —(C$_1$-C$_4$)alkyl, —(C$_2$-C$_4$)alkenyl, or —(C$_2$-C$_4$)alkynyl. Preferred such embodiments are those wherein R$_3$ is H, methyl, ethyl or propyl, more preferably H.

In certain embodiments, the present invention provides a conjugate of the formula II, wherein n is 3, 4 or 5, preferably 3; or m is 1, 2 or 3, preferably 1.

In certain embodiments, the present invention provides a conjugate of the formula II, wherein R$_4$ is —NH—CO—(CH$_2$)$_p$— or —NH—CO—NH—(CH$_2$)$_p$—, wherein p is an integer of 0-8.

In certain embodiments, the present invention provides a conjugate of the formula II, wherein R$_5$ is a polymer moiety, more specifically a biocompatible and biodegradable water-soluble polymer moiety. Such a polymer may be selected from a linear or branched PEG or copolymers thereof; a pseudo PEG interrupted by at least one group, each independently preferably selected from —NH—CO—, —CO—NH—, or (C$_3$-C$_8$)alkylene interrupted by at least two groups each independently selected from —NH—CO— or —CO—NH—; poly(lactic acid) or copolymers thereof; polyesters selected from polylactide (PLA), polyglycolide (PGA), polycaprolactone (PCL) or copolymers thereof; or polyamides based on polymethacrylamide or copolymers thereof.

The term "pseudo PEG" as used herein refers to a hydrophilic chain having great structural similarities with the PEG chain, which differs via the presence of one or more, e.g., one, two, three, four or more, groups such as ester (—CO—O—, —O—CO—), amide (—CO—NH—, —NH—CO—), carbamate (—O—CO—NH—, —NH—CO—O—), urea (—NH—CO—NH—), and (C$_3$-C$_8$)alkylene interrupted by at least two groups each independently selected from ester, amide, carbamate and urea, within it. According to the present invention, the "pseudo PEG" may in fact consist of either a sole PEG chain interrupted as defined above, or two or more separate PEG chains wherein each couple of those PEG chains are linked to each other via a group such as those listed above.

In particular such embodiments, R$_5$ is a polymer moiety, and said polymer is a linear or branched PEG, or a pseudo PEG interrupted by at least one group each independently selected from —NH—CO—, —CO—NH—, or (C$_3$-C$_8$) alkylene interrupted by at least two groups each independently selected from —NH—CO— or —CO—NH—, preferably wherein said PEG or pseudo PEG has a molecular weight of 150-20000 Da (PEG/pseudo PEG$_{150}$ to PEG/pseudo PEG$_{20,000}$), more preferably 500-2000 Da (PEG/pseudo PEG$_{500}$-PEG/pseudo PEG$_{2000}$) or 500-1000 Da (PEG/pseudo PEG$_{500}$-PEG/pseudo PEG$_{1000}$), e.g., a pseudo PEG having the structure (—CH$_2$—CH$_2$—O)$_3$—(CH$_2$)$_3$—NH—CO—(CH$_2$)$_2$—CO—NH—(CH$_2$)$_3$—(O—CH$_2$—CH$_2$—)$_3$ as exemplified herein, i.e., a pseudo PEG consisting of two separate PEG chains linked via an interrupted (C$_8$)alkylene chain of the formula —(CH$_2$)$_3$—NH—CO—(CH$_2$)$_2$—CO—NH—(CH$_2$)$_3$—.

In certain embodiments, the present invention provides a conjugate of the formula II, wherein R$_5$ is a protein moiety, and said protein is albumin such as human serum albumin (HSA), a modified albumin such as a cationized bovine serum albumin (CBSA) or a cationized human serum albumin (CHSA), or a protein containing globin-like domains having long half-life in circulation such as hemoglobin A or S.

In certain embodiments, the present invention provides a conjugate of the formula II, wherein R$_5$ is a peptide moiety, e.g., an oligopeptide or polypeptide.

The term "peptide" as used herein refers to a chain of amino acid monomers (residues) linked by peptide bonds, i.e., the covalent bond formed when a carboxyl group of one amino acid reacts with an amino group of another. Such peptides include oligopeptides and polypeptides, as well as peptides consisting of more than 50 amino acid monomers that are, in fact, proteins of low or medium molecular weight.

In certain embodiments, the peptide is a dipeptide, tripeptide or tetrapeptide consisting of 2, 3 or 4 amino acid residues, respectively, or consists of 5-50, 5-40, 5-30, 5-20, 5-15, or 5-10 amino acid residues and configured as a linear peptide, cyclic peptide, bicyclic peptide or a combination thereof. In more particular such embodiments, said peptide is a polypeptide consisting of 5, 6, 7, 8, 9, 10, 11, 12, 13, 14 or 15 amino acid residues. All such peptides may consist of residues of both natural and non-natural amino acids.

The term "amino acid" as used herein refers to an organic compound comprising both amine and carboxylic acid functional groups, which may be either a natural or non-natural amino acid. The twenty two natural amino acids are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of non-natural amino acids include diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, p-propargly-oxy-phenylalanine, m-ethynyl-phenylalanine, p-bromophenylalanine, p-iodophenylalanine, p-azidophenylalanine, p-acetylphenylalanine, azidonorleucine, 6-ethynyl-tryptophan, 5-ethynyl-tryptophan, 3-(6-chloroindolyl) alanine, 3-(6-bromoindolyl)alanine, 3-(5-bromoindolyl) alanine, azidohomoalanine, p-chlorophenylalanine, α-aminocaprylic acid, O-methyl-L-tyrosine, N-acetylgalactosamine-α-threonine, and N-acetylgalactosamine-α-serine.

In certain embodiments, the present invention provides a conjugate of the formula II, wherein R$_5$ is a carbohydrate moiety.

The term "carbohydrate" refers to a molecule containing carbon, hydrogen and oxygen atoms. The carbohydrate can be cyclic or linear, saturated or unsaturated and substituted or unsubstituted. Preferably, the carbohydrate residue comprises one or more saccharide residues. The phrase "saccharide residue" as used herein encompasses any residue of a sugar moiety, including monosaccharides, oligosaccharides and polysaccharides. Alternatively, the saccharide can be a saccharide derivative such as, but not limited to, glucosides, ethers, esters, acids and amino saccharides. Monosaccharides consist of a single sugar molecule which cannot be further decomposed by hydrolysis. Examples of monosaccharides include, without limitation, pentoses such as, but not limited to, arabinose, xylose and ribose. Oligosaccharides are chains composed of saccharide units. As commonly defined in the art and herein, oligosaccharides are composed of up to nine saccharide units. Examples of oligosaccharides include, without limitation, disaccharides such as, but not limited to, sucrose, maltose, lactose and cellobiose; trisaccharides such as, but not limited to, mannotriose, raffinose and melezitose; and tetrasaccharides such as amylopectin, Syalyl Lewis X (SiaLex) and the like. The term "polysaccharide" refers to a compound composed of at least 10 saccharide units and up to hundreds and even thousands of monosaccharide units per molecule, which are held together by glycoside bonds and range in their molecular weights from around 5,000 and up to millions of Daltons. Non-limiting examples of common polysaccharides include starch, glycogen, cellulose, gum arabic, agar and chitin.

In certain embodiments, the present invention provides a conjugate of the formula II, wherein the drug or bioactive reagent Y is selected from anticancer drugs, antineoplastic drugs, antifungal drugs, antibacterial drugs, antiviral drugs, cardiac drugs, neurological drugs, psychoactive drugs such as caffeine, drugs of abuse, alkaloids, antibiotics, bioactive peptides, steroids, steroid hormones, peptide hormones, interferons, interleukins, narcotics, nucleic acids, pesticides, or prostaglandins.

In particular such embodiments, the drug or bioactive reagent Y is an anticancer drug such as a chemotherapeutic drug, e.g., camptothecin or a derivative thereof such as 10-hydroxycamptothecin or any other camptothecin substituted at the 7-, 9- or 10-position, bosutinib, or methotrexate; an antineoplastic drug such as an alkylating antineoplastic agent, e.g., temozolomide, uramustine or bendamustine; or an antimetabolite such as methotrexate or 5-fluorouracil.

In certain embodiments, the present invention provides a conjugate of the formula H, wherein the targeting moiety is a protein, peptide, polypeptide, glycoprotein, lipoprotein, lipid, phospholipid, oligonucleotide or a mimic thereof, steroid, hormone, lymphokine, growth factor, albumin. cytokine, enzyme, coenzyme, vitamin, cofactor, human antigen, hapten, receptor protein, antibody or a fragment thereof, a substance used or modified such that it functions as a targeting moiety, or a combination thereof. Preferred such embodiments are those wherein the targeting moiety is a vitamin such as vitamin B9 (folic acid).

According to the present invention, the targeting moiety optionally composing the conjugate of the formula II is capable of binding to an extracellular antigen. Such an extracellular antigen may be any antigen presented on the membrane of a mammalian cell, more particularly a human cell. Particular such extracellular antigens are cancer antigens, i.e., tumor-specific antigens (TSA, which are present only on tumor cells) or tumor-associated antigens (TAA, which are present on some tumor cells and also some normal cells) such as, without being limited to, epidermal growth factor receptor (EGFR; ErbB-1; HER1 in humans), human epidermal growth factor receptor 2 (HER2), or prostate specific membrane antigen (PSMA).

In certain embodiments, the present invention provides a conjugate of the formula II as defined in any one of the embodiments above, wherein $R_1$ and $R_2$ each independently is H, halogen, —$OR_3$, —CO—$R_3$, —CO—$OR_3$, —OCO—$OR_3$, —OCO—$N(R_3)_2$, —CN, —$NO_2$, —$SR_3$, —$N(R_3)_2$, —CO—$N(R_3)_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl, wherein $R_3$ is H, —($C_1$-$C_4$)alkyl, —($C_2$-$C_4$)alkenyl, or —($C_2$-$C_4$)alkynyl, preferably H, methyl, ethyl or propyl; n is 3, 4 or 5, preferably 3; m is 1, 2 or 3, preferably 1; $R_4$ is —NH—CO—$(CH_2)_p$ or —NH—CO—NH—$(CH_2)_p$; and $R_5$ is a PEG moiety or a pseudo PEG interrupted by at least one group each independently selected from —NH—CO—, —CO—NH—, or ($C_3$-$C_8$) alkylene interrupted by at least two groups each independently selected from —NH—CO— or —CO—NH—, preferably wherein said PEG or pseudo PEG has a molecular weight of 150-20000, more preferably 500-2000 or 500-1000. Particular such embodiments are those wherein $R_1$ and $R_2$ each independently is H, halogen, —OH, —COH, —COOH, —OCOOH, —OCO—$NH_2$, —CN, —$NO_2$, —SH, —$NH_2$, —CO—$NH_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl; n is 3; and m is 1. In more particular such embodiments, $R_1$ and $R_2$ are H; and/or $R_5$ is a PEG moiety or a pseudo PEG moiety having the structure (—$CH_2$—$CH_2$—O)$_3$—($CH_2$)$_3$—NH—CO—($CH_2$)$_2$—CO—NH—($CH_2$)$_3$—(O—$CH_2$—$CH_2$—)$_3$, i.e., a pseudo PEG consisting of two separate PEG chains linked via an interrupted ($C_8$)alkylene chain of the formula —($CH_2$)$_3$—NH—CO—($CH_2$)$_2$—CO—NH—($CH_2$)$_3$—.

In certain particular such embodiments, $R_6$ is a divalent radical and T is a targeting moiety capable of binding to an extracellular antigen. More particular such embodiments are those wherein $R_6$ is ($CH_2$)$_y$—NH—, preferably wherein y is 1 or 2; and said targeting moiety is folic acid linked via a carboxylic group thereof, i.e., through its alpha ($\alpha$)- or gamma ($\gamma$)-carboxyl group but preferably through its $\gamma$-carboxyl group. More specific such embodiments are those wherein (i) $R_4$ is —NH—CO—NH—$CH_2$—; $R_5$ is a pseudo PEG moiety having the structure (—$CH_2$—$CH_2$—O)$_3$—($CH_2$)$_3$—NH—CO—($CH_2$)$_2$—CO—NH—($CH_2$)$_3$—(O—$CH_2$—$CH_2$—)$_3$; $R_6$ is —($CH_2$)—NH—; and Y is camptothecin or a derivative thereof such as 10-hydroxycamptothecin, temozolomide, bosutinib, or methotrexate; (ii) $R_4$ is —NH—CO—$CH_2$—; $R_5$ is a pseudo PEG moiety having the structure (—$CH_2$—$CH_2$—O)$_3$—($CH_2$)$_3$—NH—CO—($CH_2$)$_2$—CO—NH—($CH_2$)$_3$—(O—$CH_2$—$CH_2$—)$_3$; $R_6$ is —($CH_2$)—NH—; and Y is camptothecin or a derivative thereof such as 10-hydroxycamptothecin, temozolomide, bosutinib, or methotrexate; or (iii) $R_4$ is —NH—CO—; $R_5$ is a PEG moiety having the structure (—$CH_2$—$CH_2$—O)$_3$—; $R_6$ is —($CH_2$)$_2$—NH—; and Y is camptothecin or a derivative thereof such as 10-hydroxycamptothecin, temozolomide, bosutinib, or methotrexate.

In other particular such embodiments, $R_6$ is H, —($CH_2$)$_y$—OH, —($CH_2$)$_y$—SH, —($CH_2$)$_y$—$NH_2$, —($CH_2$)$_y$—COOH or —($CH_2$)$_y$—$SO_3$H, preferably —($CH_2$)$_y$—SH, —($CH_2$)$_y$—$NH_2$, —($CH_2$)$_y$—COOH, and T is absent. More particular such embodiments are those wherein y is 1, 2 or 3.

As shown in the Example section herein, the conjugate of the formula II can be prepared, e.g., by condensing a drug derivative of the formula I with a targeting moiety linked to a linker having a terminal semicarbazide (—NH—CO—NH—$NH_2$) group, under acidic conditions, thus reacting said semicarbazide group with the ketone group of said drug derivative, and purifying the conjugate obtained, e.g., by HPLC. PEG- and pseudo PEG-based linker having a terminal semicarbazide group can be prepared according to any technology or procedure known in the art, e.g., as described with respect to the pseudo PEG-based linker exemplified herein, having the structure (—$CH_2$—$CH_2$—O)$_3$—($CH_2$)$_3$—NH—CO—($CH_2$)$_2$—CO—NH—($CH_2$)$_3$—(O—$CH_2$—$CH_2$—)$_3$. The conjugate obtained by this process can thus be represented as a drug derivative-linker-targeting moiety triconjugate, wherein said linker is in fact represented by the sequence —$R_4$-$R_5$-$R_6$— in the formula I, wherein $R_4$ is the —NH—CO—NH—$(CH_2)_p$— of the semicarbazide group forming an acid labile hydrazone linkage with the drug derivative of the formula I, and $R_6$ comprises a functional group through which said linker is linked to the targeting moiety. As stated above, when a stable linkage between the targeting moiety and the linker is required, the oxime ligation could also be used to link between the ketone group of the drug derivative and an amine-oxy derivative.

In a further aspect, the present invention provides a pharmaceutical composition comprising a pharmaceutically acceptable carrier and an active agent as referred to herein, i.e., either a compound of the formula I as defined in any one of the embodiments above wherein X is not carbonyl, i.e., a prodrug of the formula Ib; or a conjugate of the formula II as defined in any one of the embodiments above, or a pharmaceutically acceptable salt thereof.

The pharmaceutical compositions of the present invention can be provided in a variety of formulations, e.g., in a pharmaceutically acceptable form and/or in a salt form, as well as in a variety of dosages.

In one embodiment, the pharmaceutical composition of the present invention comprises a non-toxic pharmaceutically acceptable salt of a compound of the formula Ib; or a conjugate of the general formula II. Suitable pharmaceutically acceptable salts include acid addition salts such as, without being limited to, the mesylate salt, the maleate salt, the fumarate salt, the tartrate salt, the hydrochloride salt, the hydrobromide salt, the esylate salt, the p-toluenesulfonate salt, the benzenesulfonate salt, the benzoate salt, the acetate salt, the phosphate salt, the sulfate salt, the citrate salt, the carbonate salt, and the succinate salt. Additional pharmaceutically acceptable salts include salts of ammonium ($NH_4^+$) or an organic cation derived from an amine of the formula $R_4N^+$, wherein each one of the Rs independently is selected from H, $C_1$-$C_{22}$, preferably $C_1$-$C_6$ alkyl, such as methyl, ethyl, propyl, isopropyl, n-butyl, sec-butyl, isobutyl, tert-butyl, n-pentyl, 2,2-dimethylpropyl, in-hexyl, and the like, phenyl, or heteroaryl such as pyridyl, imidazolyl, pyrimidinyl, and the like, or two of the Rs together with the nitrogen atom to which they are attached form a 3-7 membered ring optionally containing a further heteroatom selected from N, S and O, such as pyrrolydine, piperidine and morpholine. Furthermore, where the compounds of the formula Ib or conjugates of the formula II carry an acidic moiety, suitable pharmaceutically acceptable salts thereof may include metal salts such as alkali metal salts, e.g., lithium, sodium or potassium sails, and alkaline earth metal salts. e.g., calcium or magnesium salts.

Further pharmaceutically acceptable salts include salts of a cationic lipid or a mixture of cationic lipids. Cationic lipids are often mixed with neutral lipids prior to use as delivery agents. Neutral lipids include, but are not limited to, lecithins; phosphatidylethanolamine; diacyl phosphatidylethanolamines such as dioleoyl phosphatidylethanolamine, dipalmitoyl phosphatidylethanolamine, palmitoyloleoyl phosphatidylethanolamine and distearoyl phosphatidylethanolamine; phosphatidylcholine; diacyl phosphatidylcholines such as dioleoyl phosphatidylcholine, dipalmitoyl phosphatidylcholine, palmitoyloleoyl phosphatidylcholine and distearoyl phosphatidylcholine; phosphatidylglycerol; diacyl phosphatidylglycerols such as dioleoyl phosphatidylglycerol, dipalmitoyl phosphatidylglycerol and distearoyl phosphatidylglycerol; phosphatidylserine; diacyl phosphatidylserines such as dioleoyl- or dipalmitoyl phosphatidylserine; and diphosphatidylglycerols; fatty acid esters; glycerol esters; sphingolipids; cardiolipin; cerebrosides; ceramides; and mixtures thereof. Neutral lipids also include cholesterol and other 3β hydroxy-sterols.

Examples of cationic lipid compounds include, without being limited to, Lipofectin® (Life Technologies. Burlington, Ontario) (1:1 (w/w) formulation of the cationic lipid N-[1-(2,3-dioleyloxy)propyl]-N,N,N-trimethylammonium chloride and dioleoylphosphatidyl-ethanolamine); Lipofectamine™ (Life Technologies. Burlington, Ontario) (3:1 (w/w) formulation of polycationic lipid 2,3-dioleyloxy-N-[2(spermine-carboxamido)ethyl]-N,N-dimethyl-1-propanamin-iumtrifluoroacetate and dioleoylphosphatidyl-ethanolamine), Lipofectamine Plus (Life Technologies, Burlington, Ontario) (Lipofectamine and Plus reagent), Lipofectamine 2000 (Life Technologies, Burlington, Ontario) (Cationic lipid), Effectene (Qiagen, Mississauga, Ontario) (Non liposomal lipid formulation). Metafectene (Biontex. Munich, Germany) (Polycationic lipid), Eu-fectins (Promega Biosciences, San Luis Obispo, Calif.) (ethanolic cationic lipids numbers 1 through 12: $C_{52}H_{106}N_6O_4 \cdot 4CF_3CO_2H$, $C_{88}H_{178}N_8O_4S_2 \cdot 4CF_3CO_2H$, $C_{40}H_{84}NO_3P \cdot CF_3CO_2H$, $C_{50}H_{103}N_7O_3 \cdot 4CF_3CO_2H$, $C_{55}H_{116}N_8O_2 \cdot 6CF_3CO_2H$, $C_{49}H_{102}N_6O_3 \cdot 4CF_3CO_2H$, $C_{44}H_{89}N_5O_3 \cdot 2CF_3CO_2H$, $C_{100}H_{206}N_{12}O_4S_2 \cdot 8CF_3CO_2H$, $C_{162}H_{330}N_{22}O_9 \cdot 13CF_3CO_2H$, $C_{43}H_{88}N_4O_2 \cdot 2CF_3CO_2H$, $C_{43}H_{88}N_4O_3 \cdot 2CF_3CO_2H$, $C_{41}H_{78}NO_8P$); Cytofectene (Bio-Rad, Hercules, Calif.) (mixture of a cationic lipid and a neutral lipid). GenePORTER® (Gene Therapy Systems, San Diego, Calif.) (formulation of a neutral lipid (Dope) and a cationic lipid) and FuGENE 6 (Roche Molecular Biochemicals, Indianapolis, Ind.) (Multi-component lipid based non-liposomal reagent).

The pharmaceutically acceptable salts of the present invention may be formed by conventional means, e.g., by reacting a free base form of the active agent with one or more equivalents of the appropriate acid in a solvent or medium in which the salt is insoluble, or in a solvent such as water which is removed in vacuo or by freeze drying, or by exchanging the anion/cation of an existing salt for another anion/cation on a suitable ion exchange resin.

The pharmaceutical compositions provided by the present invention may be prepared by conventional techniques, e.g., as described in Remington: The Science and Practice of Pharmacy, $19^{th}$ Ed., 1995. The compositions can be prepared, e.g., by uniformly and intimately bringing the active agent into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients. In one embodiment, the pharmaceutical composition of the present invention is formulated as nanoparticles.

The compositions can be formulated for any suitable route of administration, but they are preferably formulated for parenteral, e.g., intravenous, intraarterial, intramuscular, intraperitoneal, intrathecal, intrapleural, intratracheal, subcutaneous, or topical administration, as well as for inhalation. The dosage will depend on the state of the patient, i.e., individual treated, and will be determined as deemed appropriate by the practitioner.

The pharmaceutical composition of the invention may be in the form of a sterile injectable aqueous or oleagenous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution, PEG, 2-hydroxypropyl-β-cyclodextrin (HPCD), Tween-80, and isotonic sodium chloride solution.

Pharmaceutical compositions according to the present invention, when formulated for inhalation, may be administered utilizing any suitable device known in the art, such as metered dose inhalers, liquid nebulizers, dry powder inhalers, sprayers, thermal vaporizers, electrohydrodynamic aerosolizers, and the like.

Pharmaceutical compositions according to the present invention, when formulated for administration route other than parenteral administration, may be in a form suitable for oral use, e.g., as tablets, troches, lozenges, aqueous, or oily suspensions, dispersible powders or granules, emulsions, hard or soft capsules, or syrups or elixirs.

Pharmaceutical compositions intended for oral administration may be formulated so as to inhibit the release of the active agent in the stomach, i.e., delay the release of the active agent until at least a portion of the dosage form has traversed the stomach, in order to avoid the acidity of the gastric contents from hydrolyzing the active agent. Particular such compositions are those wherein the active agent is coated by a pH-dependent enteric-coating polymer. Examples of pH-dependent enteric-coating polymer include, without being limited to, Eudragit® S (poly(methacrylicacid, methylmethacrylate), 1:2), Eudragit® L 55 (poly (methacrylicacid, ethylacrylate), 1:1), Kollicoat® (poly (methacrylicacid, ethylacrylate), 1:1), hydroxypropyl methylcellulose phthalate (HPMCP), alginates, carboxymethylcellulose, and combinations thereof. The pH-dependent enteric-coating polymer may be present in the composition in an amount from about 10% to about 95% by weight of the entire composition.

Pharmaceutical compositions intended for oral administration may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. The tablets may be either uncoated or coated utilizing known techniques to delay disintegration and absorption in the gastrointestinal tract and thereby provide a sustained action over a longer period. For example, a time delay material such as glyceryl monostearate or glyceryl distearate may be employed. They may also be coated using the techniques described in the U.S. Pat. Nos. 4,256,108, 4,166,452 and 4,265,874 to form osmotic therapeutic tablets for control release. The pharmaceutical composition of the invention may also be in the form of oil-in-water emulsion.

The pharmaceutical compositions of the invention may be formulated for controlled release, i.e., extended- or sustained-release, of the active agent. Such compositions may be formulated as controlled-release matrix. e.g., as controlled-release matrix tablets in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel. e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other configurations, the compositions comprise the active agent formulated for controlled release in microencapsulated dosage form, in which small droplets of the active agent are surrounded by a coating or a membrane to form particles in the range of a few micrometers to a few millimeters.

Another contemplated formulation is depot systems, based on biodegradable polymers, wherein as the polymer degrades, the active ingredient is slowly released. The most common class of biodegradable polymers is the hydrolytically labile polyesters prepared from lactic acid, glycolic acid, or combinations of these two molecules. Polymers prepared from these individual monomers include poly (D,L-lactide) (PLA), poly (glycolide) (PGA), and the copolymer poly (D,L-lactide-co-glycolide) (PLG).

The active agent as referred to herein, as well as the pharmaceutical composition thereof, can be used for prevention, treatment of management of various diseases, disorders or indications treatable by administration of the drug or a bioactive reagent Y composing said active agent.

In yet another aspect, the present invention thus relates, e.g., to a method for treatment of a cancer in an individual in need thereof, comprising administering to said individual a therapeutically effective amount of a conjugate of the formula II as defined in any one of the embodiments above, or a pharmaceutically acceptable salt thereof, wherein Y is an anticancer drug, e.g., a chemotherapeutic drug such as camptothecin or a derivative thereof, bosutinib or methotrexate, or an antineoplastic drug, e.g., an alkylating antineoplastic agent such as temozolomide, uramustine or bendamustine; and said targeting moiety is capable of binding to an extracellular antigen present on the cells of said cancer. In a particular embodiment, the cancer treated by this method is characterized by folate receptor overexpressing cells, and said targeting moiety is folic acid linked via a carboxylic group thereof, preferably through its gamma-carboxyl group. In a more particular embodiment, said cancer is carcinoma.

In still another aspect, the present invention relates to a conjugate of the formula II as defined in any one of the embodiments above, or a pharmaceutically acceptable salt thereof, wherein Y is an anticancer drug or an antineoplastic drug, and said targeting moiety is capable of binding to an extracellular antigen present on the cells of said cancer, for use in the treatment of a cancer. In a particular embodiment, the conjugate is used in the treatment of a cancer characterized by folate receptor overexpressing cells. e.g., a carcinoma, wherein said targeting moiety is folic acid linked via a carboxylic group thereof, preferably through its gamma-carboxyl group.

The invention will now be illustrated by the following non-limiting Examples.

EXAMPLES

Synthesis Schemes and Experimental Procedures
Materials and Methods

All reactions requiring anhydrous conditions were performed under argon atmosphere. All reactions were carried out at room temperature unless stated otherwise. Chemicals and solvents were either standard analytical grade (A.R. grade) or purified by standard techniques. TLC: silica gel plates Merck 60 $F_{254}$, compounds were visualized by irradiation with UV light. Flash chromatography: silica gel Merck 60 (particle size 0.040-0.063 mm), eluent given in parentheses HPLC: C18 5µ, 250×4.6 mm, eluent given in parentheses. Preparative HPLC: C18 5µ, 250×21 mm, eluent given in parentheses. ¹H-NMR and ¹³C-NMR spectra were measured using Bruker Avance operated at 400 MHz as mentioned. All general reagents, including salts and solvents, were purchased from Sigma-Aldrich. Absorption and fluorescence spectra were recorded on Spectramax-M2 fluorescent spectrometer using quartz cuvettes or quartz 96-wells plate reader.

Compound 1c

Mercaptopyridine was reacted with bromodifluoromethyl diethylphosphonate under basic conditions. The non-isolated thio-pyridine product was oxidized using sodium periodate to afford the sulfonyl-pyridine derivative 1a.

Pentaiodoacetal 1b was prepared first by replacement reaction of 5-chloro-2-pentanone with sodium iodide in acetone. The carbonyl group of 5-iodo-2-pentanone was protected with ethylene glycol catalyzed by PTSA.

As depicted in Scheme 2, to a flask equipped with a magnetic stirrer. HMPA (4 mL) was added under $N_2$ atmosphere to a solution of 2-(difluoromethylsulfonyl)-pyridine (1.5 g, 7.8 mmol, 1.0 equiv.) in THF (50 mL). The reaction mixture was cooled to −98° C. ($CH_3OH$/liquid nitrogen bath), then 2-methyl-2-(3-iodo)-propyl-1,3-dioxolane (3.15 mL, 0.0194, 2.5 equiv.) was added. A THF solution of LHMDS (2.72 mL, 3.5 equiv.) was added dropwise over 35 minute. After 30 minutes, the reaction mixture was quenched with saturated aqueous $NH_4Cl$ solution (2 mL) at −98° C. The cold bath was removed and distilled water (1 mL) was added. The mixture was extracted with EtOAc. The combined organic solution was treated with saturated aqueous NaCl to remove HMPA and dried over $Na_2SO_4$. The solvent was removed under reduced pressure to obtain a crude product which was purified by flash column chromatography (EtOAc/Hex) to give a pure product 1c (1.67 g, 67% yield) as a light yellow viscous oil. ¹H NMR (400 MHz, $CDCl_3$): δ 8.90-8.84 (m, 1H), 8.17 (dd, J=7.9, 0.7 Hz, 1H), 8.04 (td, J=7.8, 1.6 Hz, 1H), 7.67 (ddd, J=7.7, 4.7, 1.0 Hz, 1H), 4.01-3.85 (m, 2H), 2.58-2.31 (m, 2H), 1.81-1.71 (m, 4H), 1.32 (s, 3H). ¹³C NMR (101 MHz, $CDCl_3$) δ 152.65, 151.45, 139.21, 129.55, 128.55, 125.70 (t), 109.80, 65.10, 38.58, 30.78 (t), 24.25, 16.07. MS (ESI+) m/z: 322.

Ketal Sulfinate 1

As depicted in Scheme 2, sodium ethanethiol (1.2 g, 14.3 mmol, 3 equiv) was dissolved in THF (60 mL) at 0° C. under argon atmosphere and stirred at 0° C. for 5 minutes. THF (30 mL) solution of 1c (1.5 g, 4.7 mmol, 1.0 equiv.) was added. The flask was sealed with a cap and further wrapped with parafilm. The mixture was stirred at 0° C. for 2 h, then at room temperature for 10 h. The solvent was removed under vacuum, and the residue was purified by column chromatography (MeOH/DCM) to give ketal sulfinate 1 (4.1 g, 93% yield). ¹H NMR (400 MHz, DMSO-d⁶): δ 3.88-3.79 (m, 2H), 1.90-1.70 (m, 2H), 1.63-1.54 (m, 2H), 1.46 (m, 2H), 1.22 (s, 3H). ¹³C NMR (400 MHz, $CDCl_3$) δ 134.04, 131.23, 128.42, 112.76, 67.55, 41.75, 30.20, 29.99, 29.78, 26.03, 18.63. MS (ESI−) m/z: 243.

CPT-Ketone (Compound 2a)

To a solution of CPT (2, 150 mg, 0.43 mmol, 1.0 equiv.), ketal sulfinate 1 (343 mg, 1.29 equiv. 3.0 equiv.) and $ZnCl_2$ (123 mg, 0.64 mmol, 1.5 equiv.) in DCM (2.5 mL) and $H_2O$ (1 mL) was added PTSA (54 mg, 0.43 mmol, 1.0 equiv.). The reaction mixture was cooled in ice bath and TBHP (70% solution in water, 0.214 mL, 5.0 equiv.) was added dropwise with vigorous stirring. The stirring was continued at this temperature for 5 minutes. The reaction was warmed to room temperature and monitored by TLC until completion. After 24 h. a second addition of $ZnCl_2$ (123 mg, 0.64 mmol, 1.5 equiv.), ketal kulfinate 1 (343 mg, 1.29 mmole, 3.0 equiv.) and TBHP (0.214 mL 5.0 equiv.) was performed to drive the reaction further. Upon consumption of the starting material, the reaction was partitioned between DCM and saturated aqueous $NaHCO_3$ (2.0 mL). The organic layer was separated, and the aqueous layer was extracted with DCM (3×2.0 mL). The combined organic solution was dried over $Na_2SO_4$, concentrated in vacuum and purified by column chromatography to give product 2a (140 mg, 75% yield). ¹H NMR (400 MHz, $CDCl_3$): δ 8.27 (dd, J=16.1, 8.5 Hz, 2H), 7.87 (t, J=7.6 Hz, 1H), 7.79-7.65 (m, 2H), 5.46 (d, J=3.1 Hz, 2H), 2.56 (td, J=7.1, 3.6 Hz, 2H), 2.51-2.38 (m, 2H), 2.13 (s, 3H), 1.99-1.78 (m, 4H), 1.07 (t. J=7.4 Hz, 3H). MS (TOF-ESI): m/z 483.3 [M+H]⁺, 481.4 [M−H]⁻. ¹³C NMR (101 MHz, $CDCl_3$) δ 208.01, 174.62, 158.13, 153.28, 150.80, 150.66, 146.25, 137.89, 131.68, 131.31, 129.62, 126.67, 125.41, 124.60, 119.87, 98.75, 73.45, 67.10, 52.04, 42.86, 38.69, 32.34, 30.70, 30.42, 16.91, 8.54. MS (ESI+) m/z: 483, 405 [M+Na].

10-Hydroxy CPT-Ketone

Using the synthetic procedure described above for CPT-ketone, an analogue of 10-hydroxy CPT-ketone, a compound having a similarity to the SN-38 anti-cancer drug, can be prepared.

TMZ-Ketone (Compound 3a)

To a solution of TMZ (3, 25 mg, 0.13 mmol, 1.0 equiv.), ketal sulfinate 1 (120 mg, 0.45 mmol, 3.5 equiv.) and $ZnCl_2$ (31 mg, 0.22 mmol, 1.75 equiv.) in DMSO (1 mL) was added TFA (0.02 mL, 0.19 mmol, 1.5 equiv.). The reaction mixture was cooled in ice bath and TBHP (70% solution in water, 0.071 mL, 5.5 equiv.) was added dropwise with vigorous stirring. The stirring was continued at this temperature for 5 minutes. The reaction was warmed to 50° C. and monitored by HPLC. The reaction stopped after 1 h and purified by preparative HPLC to give product 3a (7 mg, 28% yield). ¹H NMR (400 MHz, $CDCl_3$) δ 7.45 (s, 1H), 7.26 (s, 1H), 6.28 (s, 1H), 4.07 (s, 3H), 2.68-2.52 (m, 4H), 2.16 (s, 3H), 1.98-1.84 (m, 2H). MS (ESI+) m/z: 329, 351 [M+Na].

Bosutinib-Ketone (Compound 4a)

To a solution of bosutinib (4, 20 mg, 0.04 mmol, 1.0 equiv.), Ketal Sulfinate 1 (30 mg, 0.11 mmol, 3 equiv.) and $ZnCl_2$ (11 mg, 0.05 mmol, 1.5 equiv.) in DMSO:$H_2O$ (0.2:0.2 mL) was added TFA (12 μL, 0.15 mmol, 4 equiv.). The reaction mixture was cooled in ice bath and TBHP (70% solution in water, 0.019 mL, 5 equiv.) was added dropwise with vigorous stirring. The stirring was continued at this temperature for 5 minutes. The reaction was warmed to 50° C. and monitored by HPLC. After 24 h, a second addition of $ZnCl_2$ (11 mg, 0.056 mmol, 1.5 equiv.), ketal sulfinate 1 (30 mg, 0.11 mmole, 3.0 equiv.) and TBHP (0.019 mL 5.0 equiv.) was performed to drive the reaction further. The reaction stopped after 24 h and purified by preparative HPLC to give product 4a (17 mg, 73% yield). ¹H NMR (400 MHz, DMSO) δ 8.16 (d, J=7.9 Hz, 1H), 7.70 (d, J=8.8 Hz, 2H), 6.71 (d, J=8.9 Hz, 2H), 5.01 (s, 1H), 4.32 (s, 1H), 3.19 (s, 2H), 2.37-2.28 (m, 3H), 2.12-1.99 (m, 4H), 1.89 (s, 1H), 1.73-1.66 (m, 1H). ¹³C NMR (101 MHz, $CDCl_3$) δ 208.68, 154.42, 153.30, 152.64, 150.51, 150.40, 145.39, 137.50, 130.74, 121.38, 118.84, 117.81, 117.62, 115.00, 114.79, 110.21, 106.11, 102.10, 91.39, 66.17, 56.66, 55.91, 54.76, 50.78, 50.09, 49.88, 49.67, 49.45, 49.24, 48.99, 43.22, 42.82, 34.87, 29.95, 24.18, 16.42. MS (ESI+) m/z: 665, 687 [M+Na].

MTX-Ketone (Compound 5a)

To a solution of MTX (5, 30 mg, 0.06 mmol, 1.0 equiv.), ketal sulfinate 1 (105 mg, 0.42 mmol, 6 equiv.) and $ZnCl_2$ (38 mg, 0.19 mmol, 3 equiv.) in DMSO (1 mL) was added PTSA (27 mg, 0.19 mmol, 3 equiv.). The reaction mixture was cooled in ice bath and TBHP (70% solution in water, 0.066 mL, 10 equiv.) was added dropwise with vigorous stirring. The stirring was continued at this temperature for 5 minutes. The reaction was warmed to 50° C. and monitored by HPLC. The reaction stopped after 24 h and purified by preparative HPLC to give product 5a (13 mg, 35% yield). $^1$H NMR (400 MHz, DMSO) δ 8.16 (d, J=7.9 Hz, 1H), 7.70 (d, J=8.8 Hz, 2H), 6.71 (d, J=8.9 Hz, 2H), 5.01 (s, 1H), 4.32 (s, 1H), 3.19 (s, 2H), 2.37-2.28 (m, 3H), 2.12-1.99 (m, 4H), 1.89 (s, 1H). 1.73-1.66 (m, 1H). $^{13}$C NMR (101 MHz, DMSO) δ 209.11, 174.97, 163.12, 152.59, 132.87, 132.71, 130.69, 129.99, 129.32, 128.06, 123.00, 122.09, 117.32, 112.18, 54.22, 52.89, 42.85, 31.58, 31.20, 30.94, 27.14, 17.36, 16.90. MS (ESI+) m/z: 589.

Compound 9

As depicted in Scheme 3, a solution of benzylchloroformate (1.3 mL 9 mmol) in DCM (20 mL) was added over 1.5 h to a solution of compound 8 (2 gr, 9 mmol) and triethyl amine (3.8 ml, 27 mmol) in DCM (40 mL) cooled at 0° C. The solution was stirred for 2 h at 0° C., then warmed to room temperature. After completion the crude was concentrated by evaporation and the product was purified by column chromatography (Hex:EtOAc) to give product 9 (1.3 gr, 40% yield). $^1$H NMR (400 MHz, CDCl$_3$) δ 7.21-7.11 (m, 5H), 4.89 (s, 2H), 3.46-3.31 (m, 12H), 3.07 (dd, J=12.6, 6.3 Hz, 2H), 2.94 (t J=6.5 Hz, 2H), 1.84-1.76 (m, 1H), 1.64-1.56 (m, 1H). $^{13}$C NMR (101 MHz, CDCl$_3$) δ 157.58, 137.35, 129.06, 128.58, 128.47, 70.78, 70.54, 70.40, 69.63, 66.97, 50.32, 39.36, 39.16, 30.06, 27.39. MS (ESI+) m/z: 255.

Compound 10

As depicted in Scheme 3, compound 9 (100 mg, 0.28 mmol). DMAP (70 mg, 0.6 mmol) and succinic anhydride (28 mg, 0.28 mmol) were dissolved into 4 mL of DCM. The solution was stirred for 2 h. After completion, the mixture was extracted with 1 M HCl, the organic layer dried over Na$_2$SO$_4$, and concentrated to give product 10 (96 mg, 75% yield). $^1$H NMR (400 MHz, CDCl$_3$) δ 7.28-7.13 (m, 1H), 6.98 (s, 1H), 5.79 (s, 1H), 4.92 (s, 1H), 3.52-3.27 (m, 3H), 3.17-3.08 (m, 1H), 2.52-2.41 (m, 1H), 2.38-2.30 (m, 1H), 1.60 (dt, J=12.6, 6.2 Hz, 1H). $^{13}$C NMR (101 MHz, CDCl$_3$) δ 175.87, 173.23, 157.42, 137.41, 129.09, 128.61, 128.38, 70.97, 70.63, 70.56, 70.03, 69.92, 67.01, 39.54, 38.29, 31.35, 30.39, 30.05, 29.44. MS (ESI−) m/z: 425. MS (ESI+) m/z: 247.

Compound 11

As depicted in Scheme 4, in one flask, triphosgene (288 mg, 0.5 mmol, 1.2 equiv.) was dissolved in toluene (16 mL). In a separate flask, tert-butyl (2-(2-(2-aminoethoxy)ethoxy)ethyl)carbamate (200 mg, 0.4 mmol, 1 equiv.) was dissolved in toluene (12 mL) and the resulted solution was added dropwise within 10 minutes to the mixture in the first flask at reflux. The reaction mixture was kept at reflux for 30 minutes. The toluene was removed under reduced pressure to obtain the corresponding crude iso-cyanate intermediate product which was dissolved in a solution of toluene (10 mL). DBTL (3 drops) and tert-butyl carbazate (104 mL, 0.4 mmol, 1 equiv.), then the mixture was heated to reflux for 30 minutes and monitored by TLC (Hex:EtOAc). The toluene was removed under vacuum and the crude product was purified by column chromatography (Hex:EtOAc) to give product 11 (200 mg, 50% yield). $^1$H NMR (400 MHz, CDCl$_3$) δ 8.10-7.19 (m, 5H), 7.12 (s, 1H), 6.59 (s, 1H), 6.19 (s, 1H), 5.54 (s, 1H), 5.07 (s, 2H), 3.79-3.42 (m, 12H), 3.42-3.16 (m, 4H), 1.85-1.64 (m, 4H), 1.44 (s, 9H). $^{13}$C NMR (101 MHz, CDCl$_3$) δ 159.76, 157.36, 156.79, 137.50, 129.17, 128.83, 128.70, 81.97, 71.11, 70.88, 70.73, 70.63, 70.06, 67.16, 39.74, 39.49, 30.11, 29.65, 28.95.

Compound 12

As depicted in Scheme 4, a mixture of compound 11 (100 mg, 0.19 mmol), 5% Pd/C (cat.), and methanol was stirred under a balloon of hydrogen at ambient pressure at room temperature overnight. The reaction mixture was then filtered through a short plug of Celite and the filtrate was concentrated in vacuo to give product 12 (68 mg, 93% yield). $^1$H NMR (400 MHz, CDCl$_3$) δ 3.53 (m, 14H), 3.22 (m, 2H), 3.04 (m, 1H), 1.92 (s, 2H), 1.61 (m, 4H), 1.36 (s, 9H). $^{13}$C NMR (101 MHz, CDCl$_3$) δ 160.20, 157.36, 81.66, 71.03, 70.55, 70.20, 70.01, 42.11, 41.72, 39.83, 38.46, 30.09, 28.96, 27.92. MS (ESI+) m/z: 379, 401 [M+Na].

Compound 13

As depicted in Scheme 4, compound 12 (50 mg, 0.13 mmol), DMAP (33 mg, 0.26 mmol) and succinic anhydride (14 mg, 0.13 mmol) were dissolved into 3 mL of DCM. The solution was stirred for 2 h. After completion, the mixture was extracted with 1 M HCl, the organic layer dried over Na$_2$SO$_4$, and concentrated to give product 13 (46 mg, 70% yield). $^1$H NMR (400 MHz, CDCl$_3$) δ 3.55-3.37 (m, 12H), 3.15 (m, 2H), 2.63-2.41 (m, 4H), 2.32 (m, 2H), 1.72-1.61 (m, 4H), 1.33 (s, 9H). $^{13}$C NMR (101 MHz, CDCl$_3$) δ 177.12, 173.48, 160.94, 156.80, 82.01, 72.20, 71.09, 70.87, 70.04, 40.53, 37.40, 32.12, 31.20, 30.41, 30.08, 29.97, 29.12, 29.03. MS (ESI+) m/z: 451.

Compound 14

As depicted in Scheme 5, DMAP (68 mg, 0.55 mmol, 3 equiv.) and compound 10 (70 mg, 0.18 mmol, 1 equiv.) were dissolved in DCM (2 mL). HBTU (210 mg, 0.55 mmol, 3 equiv.) was added and the reaction mixture was stirred in room temperature for 10 minutes, then compound 13 (84 mg, 0.19 mmol, 1 equiv.) was added, and the reaction was monitored by TLC (Hex:EtOAc). After completion the product was purified by column chromatography (Hex:EtOAc), to give product 14 (97 mg, 82% yield).

Compound 15

As depicted in Scheme 5, a mixture of compound 14 (97 mg, 0.0.151 mmol), 5% Pd/C (cat.), and methanol was stirred under a balloon of hydrogen at ambient pressure at room temperature overnight. The reaction mixture was then filtered through a short plug of Celite and the filtrate was concentrated in vacuo and directly reacted.

DMAP (25 mg, 0.21 mmol, 8 equiv.) and folic acid (50 mg, 0.105 mmol, 4 equiv.) were dissolved in DMSO (4 mL). HBTU (20 mg, 0.052 mmol, 2 equiv.) was added and the reaction mixture was stirred in room temperature for 10 minutes, then compound 14a (13 mg, 0.026 mmol, 1 equiv.) was added, the reaction progress was monitored by HPLC (ACN/H$_2$O). After completion the product was purified by preparative HPLC (ACN/H$_2$O) to give product 15 (24 mg, 60% yield). $^1$H NMR (400 MHz, DMSO) δ 8.68 (s, 1H), 7.64 (d, J=6.5 Hz, 2H), 6.63 (d, J=8.7 Hz, 2H), 4.52 (s, 2H), 4.26 (d, J=9.6 Hz, 1H), 3.61-3.17 (m, 22H), 3.06 (dd, J=22.9, 6.1 Hz, 10H), 2.26-1.98 (m, 8H), 1.58 (dd, J=16.1, 9.8 Hz, 8H), 1.37 (s, 9H). $^{13}$C NMR (101 MHz, DMSO) δ 175.06, 175.06, 172.42, 172.42, 167.42, 159.59, 154.11, 154.11, 151.82, 149.35, 149.35, 130.17, 130.17, 129.16, 129.16, 112.40, 112.40, 80.11, 70.92, 70.92, 70.70, 70.70, 69.45, 69.22, 69.22, 53.39, 46.98, 38.03, 37.78, 36.95, 36.95, 33.18, 32.49, 32.02, 32.02, 31.16, 30.85, 30.53, 30.53, 29.25, 29.25, 27.70. MS (ESI+) m/z: 1223, 1245 [M+Na].

Compound 7

As depicted in Scheme 6, compound 15 was dissolved in a mixture of 2 ml DCM and 2 ml TFA, and stirred for 1 h. After completion the product was concentrated in vacuum and directly reacted in the next step.

CPT-ketone 2a (20 mg, 0.0414 mmol, 1 equiv.) was dissolved in methanol (5 mL). TFA (5 drops) and compound 15a (82 mg, 0.083 mmol, 2 equiv.) were added and the mixture was stirred for 2 hour at 40° C. The reaction progress was monitored by HPLC (ACN/H$_2$O). After completion, the crude was purified by preparative HPLC (ACN/H$_2$O) to give 7 (40 mg, 75% yield). $^1$H NMR (400 MHz, DMSO) δ 8.90 (s, 1H), 8.61 (d, J=2.2 Hz, 1H), 8.22-8.26 (m, 3H), 8.01-7.61 (m, 8H), 7.10-6.85 (m, 2H), 6.59 (m, 3H), 5.53-5.15 (m, 3H), 4.87 (s, 1H), 4.46 (d, J=4.4 Hz, 2H), 4.31 (m, 1H), 3.50 (m, 22H), 3.16-2.93 (m, 10H), 2.51 (m, 2H), 1.57 (m, 8H), 0.88 (t, J=7.1 Hz, 2H). $^{13}$C NMR (101 MHz, DMSO) δ 173.69, 172.41, 157.77, 157.41, 153.76, 151.83, 151.19, 149.99, 149.71, 145.85, 142.15, 132.77, 131.59, 131.05, 130.23, 129.92, 129.72, 129.15, 128.86, 127.60, 125.91, 124.40, 122.96, 120.26, 113.55, 112.42, 97.90, 73.57, 70.90, 70.68, 69.70, 69.21, 66.43, 51.44, 47.09, 38.33, 37.82, 36.93, 35.67, 33.34, 32.04, 31.43, 31.19, 30.51, 25.20, 19.49, 16.82, 9.97, 8.95. MS (ESI+) m/z: 1689, 1711 [M+Na].

Compound 7b

As depicted in Scheme 7, compound 13 was dissolved in a mixture of 2 ml DCM and 2 ml TFA, and mixed for 1 h. After completion the product 13a was concentrated in vacuum and directly reacted in the next step.

CPT-ketone 2a (10 mg, 0.02 mmol, 1 equiv.) was dissolved in methanol (5 mL). TFA (5 drops) and compound 13a (21 mg, 0.06 mmol, 3 equiv.) were added and the mixture was stirred for 2 hour at 40° C. The reaction progress was monitored by HPLC (ACN/H$_2$O). After completion, the crude was purified by preparative HPLC (ACN/H$_2$O) to give product 7b (8 mg, 50% yield). $^1$H NMR (400 MHz, DMSO) δ 8.89 (s, 1H), 8.24 (dd, J=18.5, 8.4 Hz, 2H), 7.95-7.87 (m, 1H), 7.78-7.67 (m, 2H), 6.54 (t, J=5.8 Hz, 1H), 5.27 (d, J=12.4 Hz, 2H), 3.72-3.35 (m, 16H), 3.12 (d, J=6.3 Hz, 2H), 2.57 (s, 4H), 2.23 (t. J=7.3 Hz, 2H), 2.10 (m, 1H), 2.02 (m, 1H), 1.89-1.53 (m, 10H), 0.85 (t, J=7.0 Hz, 3H). $^{13}$C NMR (101 MHz, DMSO) δ 178.93, 174.79, 171.67, 162.02, 157.40, 154.92, 150.04, 149.70, 141.95, 136.93, 131.46, 129.50, 128.52, 125.86, 124.15, 102.24, 100.54, 95.33, 84.25, 81.26, 70.90, 70.72, 69.70, 69.34, 59.27, 56.59, 52.43, 38.36, 37.81, 36.94, 36.74, 32.65, 31.19, 30.68, 30.28, 29.98, 29.16, 28.54, 19.52, 16.76, 10.26, 9.60. MS (ESI+) m/z: 943.

Compound 6

As depicted in Scheme 8, compound 16 (20 mg, 0.082 mole, 2 eq.) and CPT-ketone 2a (10 mg, 0.041 mole, 1 eq.) were dissolved in toluene and catalytic amount of PTSA was added. The reaction was heated to 110° C. and stirred for 5 h. The reaction progress was monitored by HPLC (ACN/H$_2$O). After completion, the crude was purified by preparative HPLC (ACN/H$_2$O) to give product 6 (15 mg, 75% yield).

$^1$H NMR (400 MHz, CDCl$_3$) δ 8.40-8.14 (m, 2H), 7.85 (d, J=1.4 Hz, 1H), 7.69 (m, 3H), 7.38-7.29 (m, 1H), 5.73 (m, 1H), 5.58-5.20 (m, 3H), 5.03-4.87 (m, 1H), 4.71-4.53 (m, 1H), 3.95 (m, 6H), 2.61-2.45 (m, 2H), 2.31-2.15 (m, 2H), 1.96-1.78 (m, 2H), 1.71-1.57 (m, 2H), 1.41 (s, 3H), 1.10-1.01 (t, 3H). $^{13}$C NMR (101 MHz, CDCl$_3$) δ 174.60, 158.12, 154.56, 153.33, 150.68, 148.71, 146.22, 139.89, 132.92, 131.76, 131.32, 130.76, 130.47, 129.61, 125.46, 124.71, 119.92, 114.80, 111.75, 111.22, 110.29, 108.94, 108.75, 98.84, 75.92, 74.66, 73.45, 71.98, 71.06, 67.08, 65.11, 57.15, 57.02, 52.05, 42.86, 39.37, 38.41, 36.66, 35.59, 34.56, 32.65, 32.33, 32.16, 31.36, 30.90, 30.42, 30.25, 30.06, 29.96, 27.94, 26.24, 25.13, 23.66, 23.42, 19.85, 17.47, 14.86, 8.54, 1.75.

Buffer Preparation Protocols:

Preparation of Acetate Buffers.

The buffer solutions were prepared by addition of acetic acid solution (pH 4, 284.4 mL; pH 4.8, 87.2 mL; pH 5, 73.4 mL; pH 6 52.4 mL) and sodium hydroxide solution (1 M, 50 mL) in 500 mL volumetric flask. The mixture was diluted with distilled water to a final volume of 500 mL.

Preparation of PBS Buffers.

1M NaH$_2$PO$_4$ solution was prepared by dissolving 13.8 g of NaH$_2$PO$_4$.H$_2$O in distilled H$_2$O to make a final volume of 100 mL. 1M Na$_2$HPO$_4$ solution was prepared by dissolving 14.2 g of Na$_2$HPO$_4$ in distilled H$_2$O to make a final volume of 100 mL. 1M NaH$_2$PO$_4$ (pH 7.0, 42.3 mL; pH 7.4, 22.6 mL) and 1M Na$_2$HPO$_4$ (pH 7.0, 57.7 mL; pH 7.4 mL) were mixed and diluted to IL with H$_2$O.

Hydrolysis of Compound 7 in Buffer: pH 4.8, pH 6.0, pH 6.5, pH 7.0 and pH 7.4.

A stock solution of 7 (10 mM) was prepared by dissolving 17.95 mg of the compound in 1 mL DMSO. A sample of 25 μL from the stock solution was added to 75 μL DMSO, and the resulting solution was added slowly while stirring to 840 μL of the appropriate buffer (pH 4.8, 6.0, 6.5, 7.0, or 7.4). Samples were taken at different times and analyzed by HPLC. The hydrolysis percentage of the carrier was calculated based on the HPLC integration ratio of the starting material and the corresponding hydrolytic products.

[$^3$H]-Folic Acid Competition Assay

KB HiFR cells (nasopharyngeal epidermal carcinoma cells overexpressing the folate receptor) were growth in folate depleted RPMI+10% FBS for 15 days in order to overexpress the folate receptor. KB cells were growth in regular RPMI+10% FBS. KB or KB HiFR cells were seeded in 24 wells/plate, 1×10$^6$ cells/well in 500 μL of folate depleted RPMI without FBS. The cells were treated as follow: 3 wells: 10 μL/well of RMPI without FBS; 3 wells: 10 μL/well of cold folic acid (100 μM, final concentration in each well 2 μM); 3 wells: 10 μL/well of compound 7 ([FA]=100 μM, final concentration in each well 2 μM); 3 wells: 10 μL/well of compound 7b ([FA]=100 μM, final concentration in each well 2 μM); 3 wells: 10 μL/well of CPT ([FA]=100 μM, final concentration in each well 2 μM). The cells were incubated for 3 hours at 37° C., 5% CO$_2$. After 3 h of incubation 10 μL of [$^3$H]-FA (5 μCi/mL, 10 μM, final concentration in each well 0.2 μM) were added to each well. After 3 h of incubation the medium was collected (100 mL were kept and added to 3 mL of scintillation fluid for counting, as reference), the cells harvested with trypsin, added to the medium and the suspension was centrifuged. The supernatant was discarded and the pellet washed 3 times with 3 mL of cold PBS. After the last wash, each sample was treated overnight with 500 μL of 0.5N NaOH, followed by neutralization with 0.5N HCl. After 30 minutes, 600 μL of the suspension was added to 3 mL of scintillation fluid and the amount of radioactivity was determined by liquid scintillation counting.

Proliferation Assay

KB HiFR were seeded in 96 well/plates, 2×10$^3$ cell/100 μL in folate depleted RPMI+10% FBS. After 24 h incubation at 37° C., 5% CO$_2$, 100 μL of serial dilutions (200-0.00002 μM CPT equivalent concentrations) of CPT and CPT-derivatives were added to the wells (final concentration 100-0.00001 μM). In the short exposure (pulse and chase) experiment the treatments were removed after 10 min incubation at 37° C., 5% CO$_2$, the cells were washed once with PBS and incubated with fresh folate depleted RPMI+10% FBS for 72 h. In the long exposure experiment, the cells were incubated for 72 h with the treatment. After 72 h incubation, 30 μL of mg/mL solution of MTT (3-(4,5-dimethylthiazol-2-yl)-2,5-diphenyltetrazolium bromide) in PBS were added to each well, and incubated for 5 h. After incubation the medium was removed and the cells lysed in 200 μL DMSO and kept under gentle stirring protected from light for 20 min. Absorbance was measured at 560 nm and survival plotted as percentage of untreated control.

Example 1

Sodium difluoroalkyl ketal sulfinate 1 is a ketone-protected reagent, capable of reacting with a heteroarene C—H bond under oxidative acidic conditions to produce the corresponding ketone derivative I (Scheme 1). Deprotection of the ketal should occur in situ under the hydrolytic acidic conditions of the reaction to afford the ketone functional group. The heteroarene-ketone analogue can be readily masked through an acid-labile hydrazone linkage (Patil et al., 2012; Yang et al., 2007) (III) or a photo-labile ketal protecting group (Gravel et al., 1983) (I).

The synthesis of ketal sulfinate 1 was achieved in an analogous manner to that recently described for other sulfinate salts (Scheme 2). Thus, alkylation of ketal 1b by pyridine derivative 1a generated sulphone 1c. The latter was reacted with sodium mercaptoethanol to afford sulfinate salt 1. This synthesis could be easily performed on multi-gram scale to produce sulfinate 1 with good yields. Heteroarene difluoroalkylation by sulfinate salt 1 to produce the corresponding ketone derivative was initially established on caffeine as a test substrate. Caffeine successfully reacted with sulfinate 1 through direct functionalization of its C—H bond to afford ketone derivative 1d in 87% yield.

TABLE 1

Difluoroalkylation by sulfinate salt 1 of CPT, TMZ, bosutinib and MTX

| Heteroarene drug | Heteroarene-ketone derivative | Isolated yield |
|---|---|---|
| 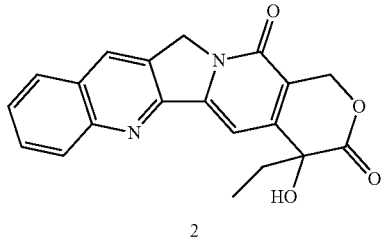 [SMILES: CCC1(O)C(=O)OCc2c1cc1n(c2=O)Cc2cc3ccccc3nc2-1]<br>2 | 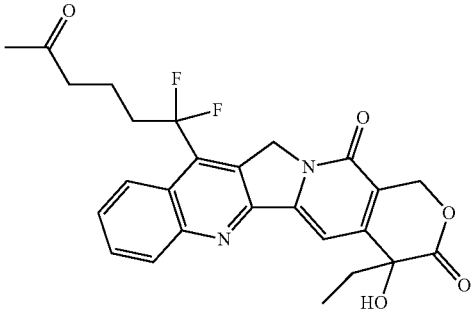<br>2a | 78% |
| 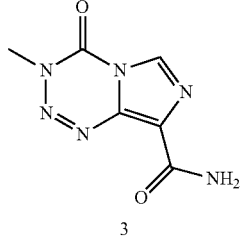<br>3 | 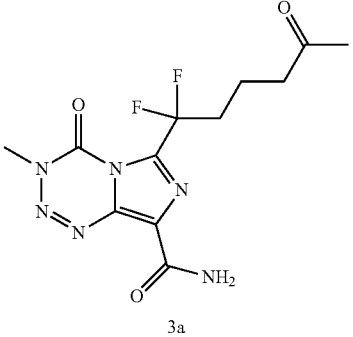 [SMILES: CC(=O)CCCC(F)(F)c1nc(C(N)=O)c2nnn(C)c(=O)n12]<br>3a | 28% |
| 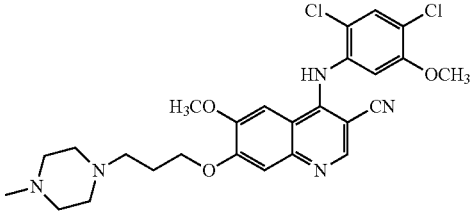<br>4 | 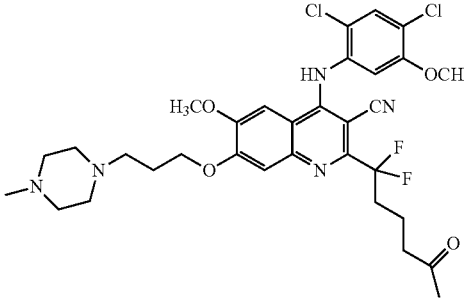<br>4a | 67% |

TABLE 1-continued

Difluoroalkylation by sulfinate salt 1 of CPT, TMZ, bosutinib and MTX

| Heteroarene drug | Heteroarene-ketone derivative | Isolated yield |
|---|---|---|
| 5 | 5a | 35% |

Next, we sought to evaluate the functionalization-capability of sulfinate salt 1 on CPT (2), TMZ (3), bosutinib (4) and MTX (5), all heteroarene known antineoplastic drugs. CPT is a topoisomerase inhibitor with limited options for bioconjugation through its tertiary hydroxyl group. TMZ is a cytotoxic alkylating agent, which is considered as an untaggable compound due to the absence of suitable functional group. Likewise, bosutinib, an approved tyrosine kinase inhibitor based drug, has no functional group available for conjugation. MTX, an antifolate-based chemotherapeutic drug, is another heteroarene with limited bioconjugation options (Table 1). The four heteroarene drugs were successfully functionalized by sulfinate salt 1 to afford the corresponding ketone analogues in moderate to good yields. For CPT, bosutinib and MTX, sulfinate salt 1 was able to selectively functionalize the heteroarenes at the most electron-deficient C—H bond.

Figure 2A:
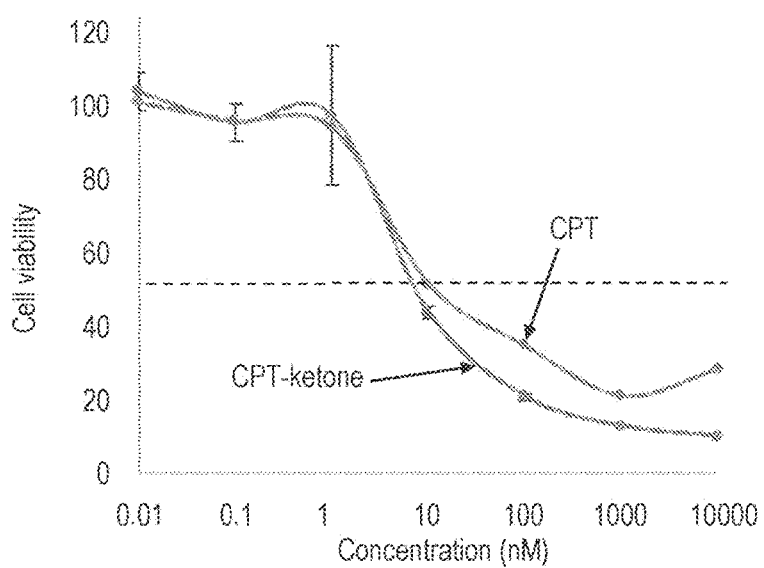
FIGS. 2A-2C show tumor cell growth inhibition assays of CPT (2A), TMZ (2B), and bosutinib (2C) vs. their ketone analogues.
Figure 2B:
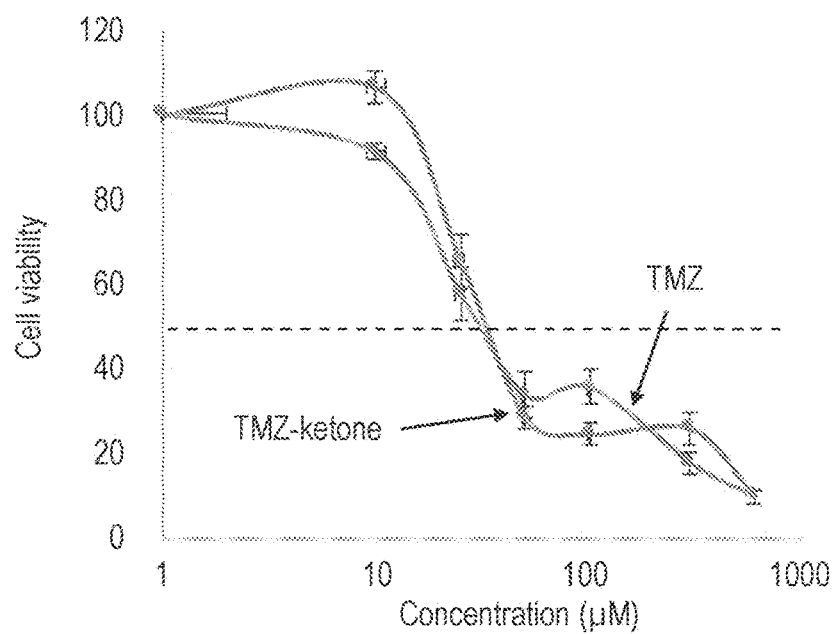
Figure 2C:
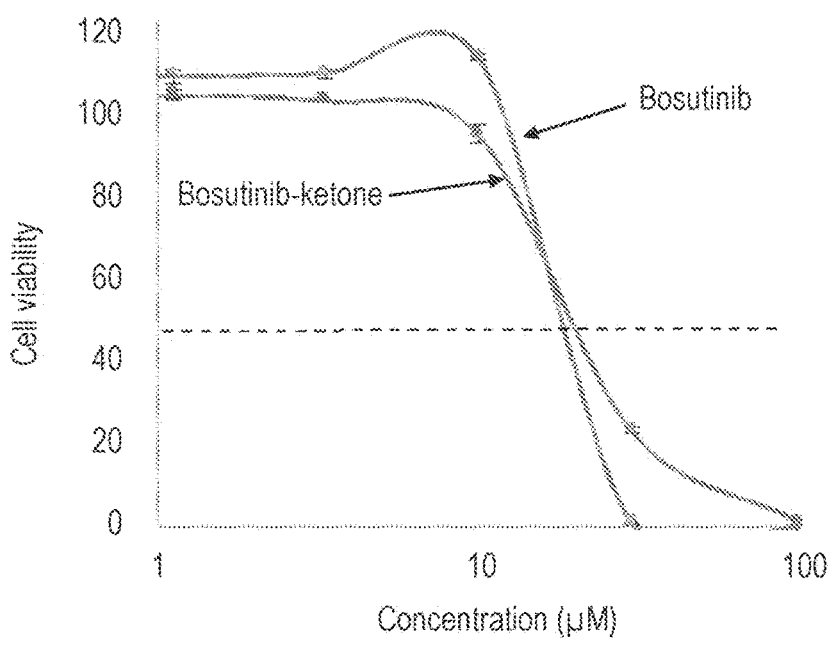

In order to find out whether the new derivatives retain their potency, the cytotoxicity of the CPT-, TMZ- and bosutinib-ketone analogues was evaluated in comparison to that of the parent drugs. FIG. 2 shows representative cell-growth inhibition plots for each drug and its ketone analogue, wherein the applied cell lines and the calculated $IC_{50}$s are presented in Table 2.

TABLE 2

$IC_{50}$s values calculated from cell-growth inhibition assays for CPT, TMZ and bosutinib, and their ketone analogues

| Drug | $IC_{50}$ | Cell line |
|---|---|---|
| CPT | 7 nm | U-87 |
| CPT-ketone | 10 nm | U-87 |
| TMZ | 36 μm | U-251 |
| TMZ-ketone | 35 μm | U-251 |
| Bosutinib | 17 μm | SF-295 |
| Bosutinib-ketone | 17 μm | SF-295 |

Figure 3:
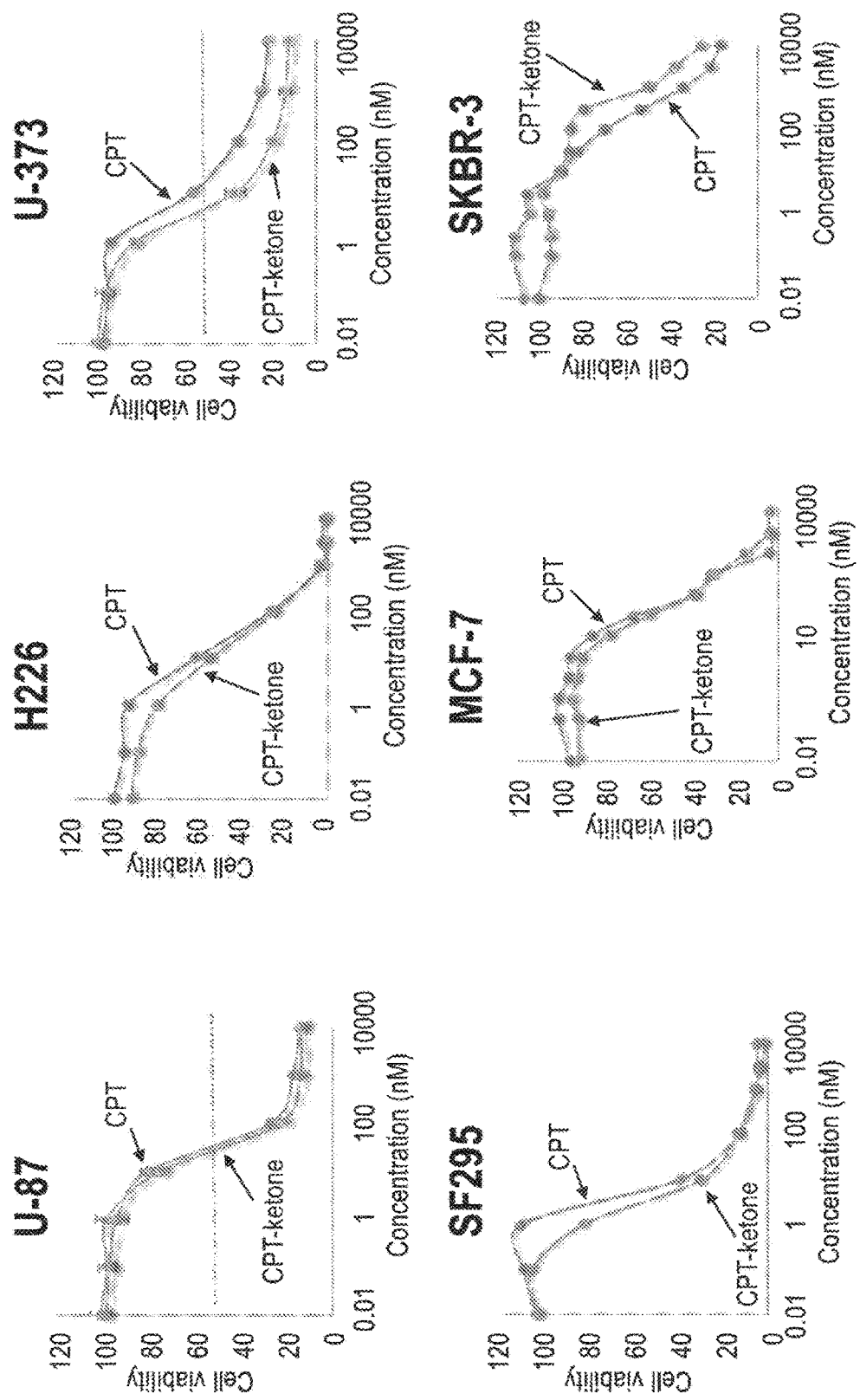
FIG. 3 shows CPT and CPT-ketone 2a cell viability assay on six different cell lines.
Figure 4:
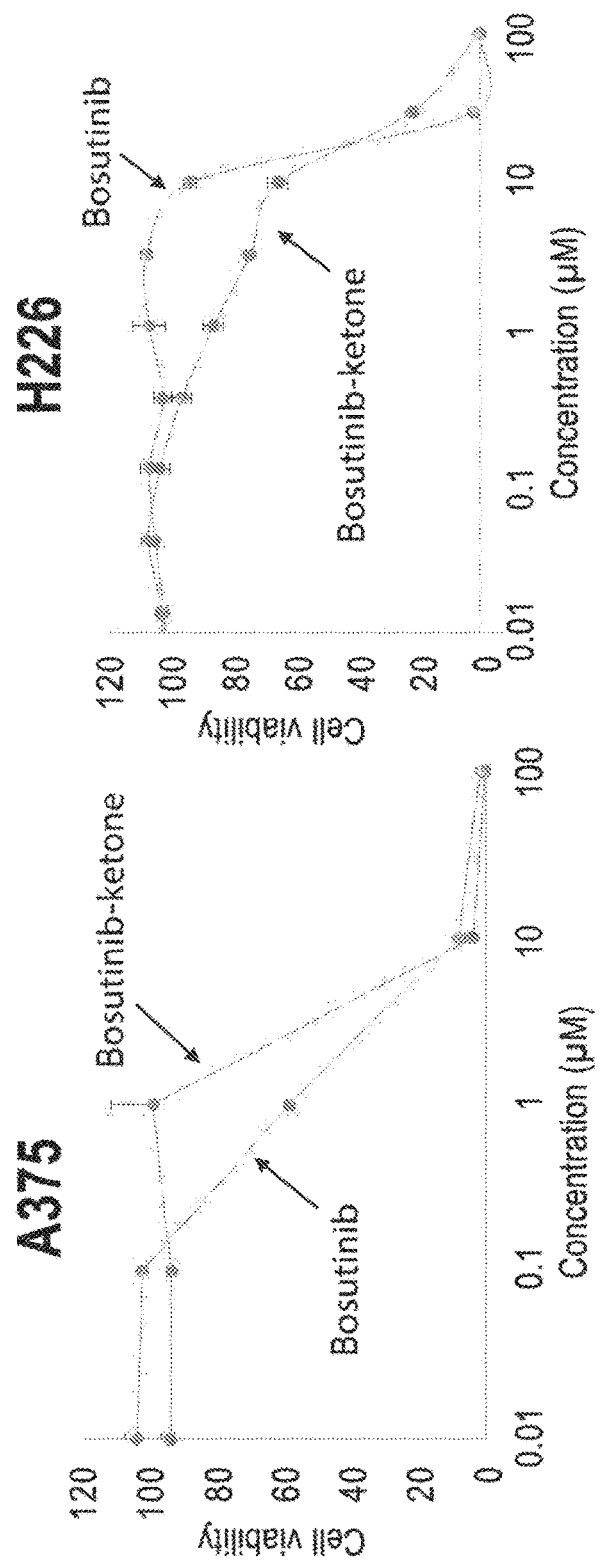
FIG. 4 shows bosutinib and bosutinib-ketone 4a cell viability assay on different cell lines.

Remarkably, for three of the four drugs, tumor cell-growth inhibition assays showed almost identical cytotoxicity ($IC_{50}$ values) for the ketone-derivatives and their native drugs. Functionalization of CPT, TMZ and bosutinib using sulfinate salt 1, resulted in ketone analogues that retained their cytotoxic activity. However, the ketone analogue of MTX completely lost its cytotoxicity. The assays were repeated with several tumorous cell-lines and the obtained results were similar (FIGS. 3-4). These results indicate that it is possible for certain biologically relevant heteroarenes to maintain their original activity, after C—H functionalization by sulfinate salt 1, at an appropriate position.

Example 2

Figure 5A:
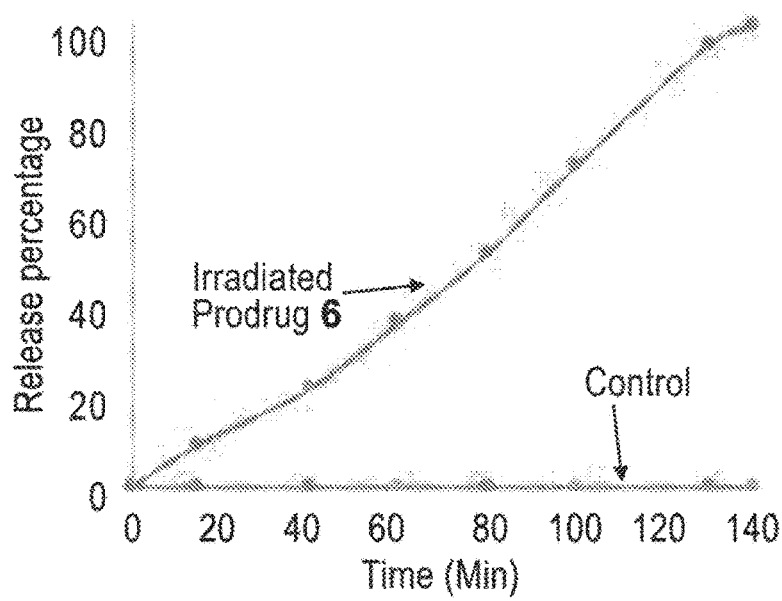
FIGS. 5A-5B show the release of CPT-ketone 2a with and without irradiation of prodrug 6 (5A); and U-87 human primary glioblastoma cell growth inhibition assay of CPT-ketone 2a, and prodrug 6 before and after irradiation (5B).
Figure 5B:
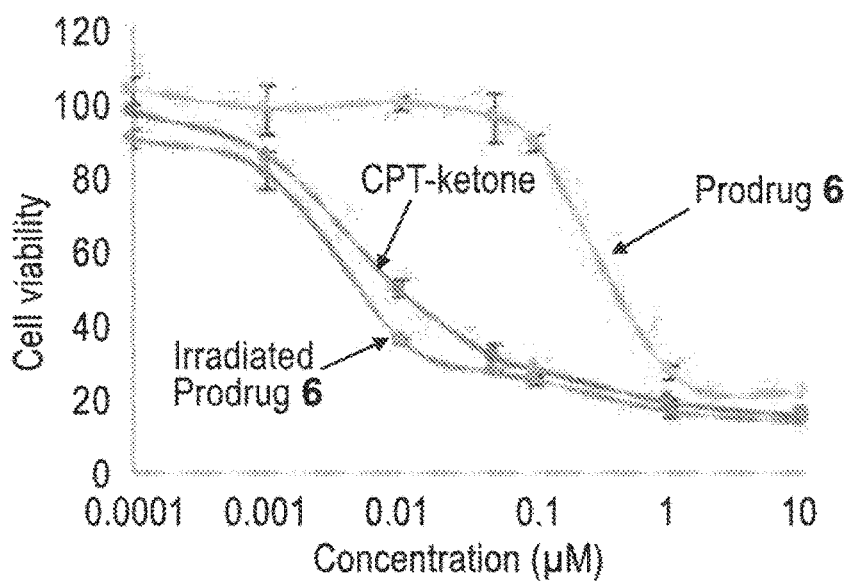

To determine the usefulness of the drug analogues produced harboring a ketone for controlled release and bioconjugation. CPT-ketone 2a was selected for further evaluation. As presented in Scheme 1, a ketone functional group can be masked either through an acid-labile hydrazone linkage or with a photo-labile ketal protecting group. CPT-ketone 2a was masked with a photo-labile protecting group (Gravel et al., 1983; Klan et al., 2013) to produce ketal derivative 6 (FIG. 5). This derivative can be considered as prodrug form of CPT-ketone 2a. Irradiation of prodrug 6 with UV light over 2 hours under physiological conditions resulted in release of CPT-ketone 2a (FIG. 5A). No release was observed without irradiation. The cytotoxicity of prodrug 6 was then evaluated in a standard cell-growth inhibition assay before and after irradiation with UV light (FIG. 5B). As expected, derivative 6 before irradiation exhibited typical prodrug behavior, with an $IC_{50}$ value of 350 nM. Prodrug 6 after irradiation has showed significantly higher cytotoxicity with an $IC_{50}$ value of 10 nM, similarly to that obtained for CPT-ketone 2a ($IC_{50}$=5 nM). These results demonstrate how the newly installed ketone of the heteroarene analogues can be used to obtain prodrugs with a photo-labile controlled-release pathway. In this example, the prodrug was activated with UV light; however, there are analogues protecting groups that can be removed through a visible or near infrared light (Lu et al., 2003). To our knowledge, this is the first demonstration of a prodrug photo-activation, which is based on unmasking of a ketone group (Klan et al., 2013).

Next, we sought to evaluate the acid-labile hydrazone linkage, for controlled-release and bioconjugation between CPT-ketone 2a and a targeting vehicle. Hydrolysis via an acid-labile linkage is a useful controlled-release mechanism for cell-penetrating vehicles such as folic acid (FA) (Zhao et al., 2008) conjugate (Scheme 9). Thus. CPT-ketone 2a was reacted with a semicarbazide derivative of folic acid (7a), via a semicarbazone linkage, to generate CPT-folic acid conjugate 7 with an acid-labile controlled-release mechanism (see Synthesis schemes and experimental procedures).

A PEG linker derivative was used as a spacer to connect between the folic acid and CPT-ketone 2a.

Example 3

Figure 6:
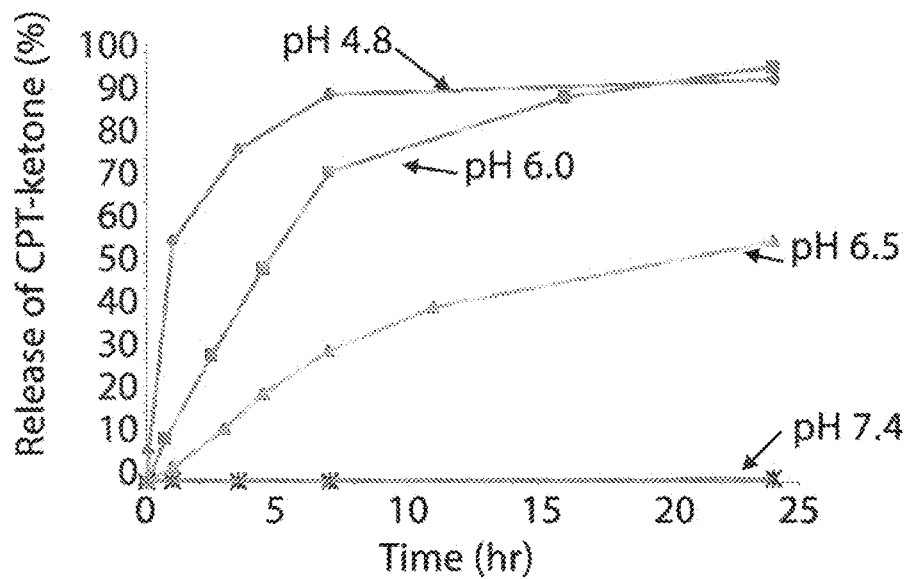
FIG. 6 shows the hydrolysis rate of CPT-ketone-semicarbazone-PEG-FA 7 as a function of time after incubation in buffer at pH 4.8, 6.0, 6.5, 7.0, and 7.4, at 37° C.

To validate the release of CPT-ketone 2a from the folate conjugate 7, we monitored the hydrolysis of the semicarbazone linkage under various pHs (physiological conditions—pH, 7.4; early endosome stage—pH, 6.5 and 6.0; and late endosome stages—pH, 4.8). The kinetic plots of CPT-ketone 2a release are presented in FIG. 6. The semicarbazone-base conjugate exhibited excellent selective hydrolysis under acidic conditions. Fast release kinetics of CPT-ketone 2a was observed under acidic pHs, while no release at all was observed over 24 hr. at physiological pH. Importantly, at relatively mild acid conditions (early-stage endosome pH, 6.5), release of CPT-ketone 2a (about 50%) still effectively took place (Yang et al., 2007).

Figure 7A:
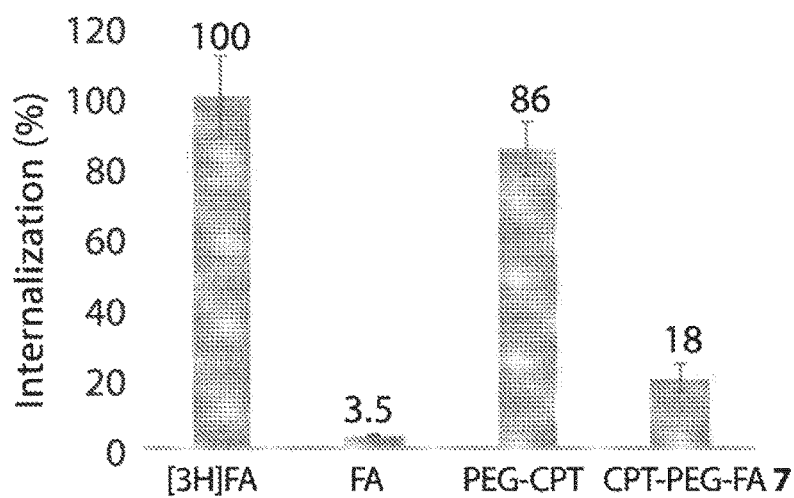
FIGS. 7A-7B show measurement of binding affinity of folate-conjugate 7 with FR receptors using high expressed-FR KB cells (7A); and cytotoxicity assay for CPT-folic acid conjugate 7 using HiFR KB cells (7B).
Figure 7B:
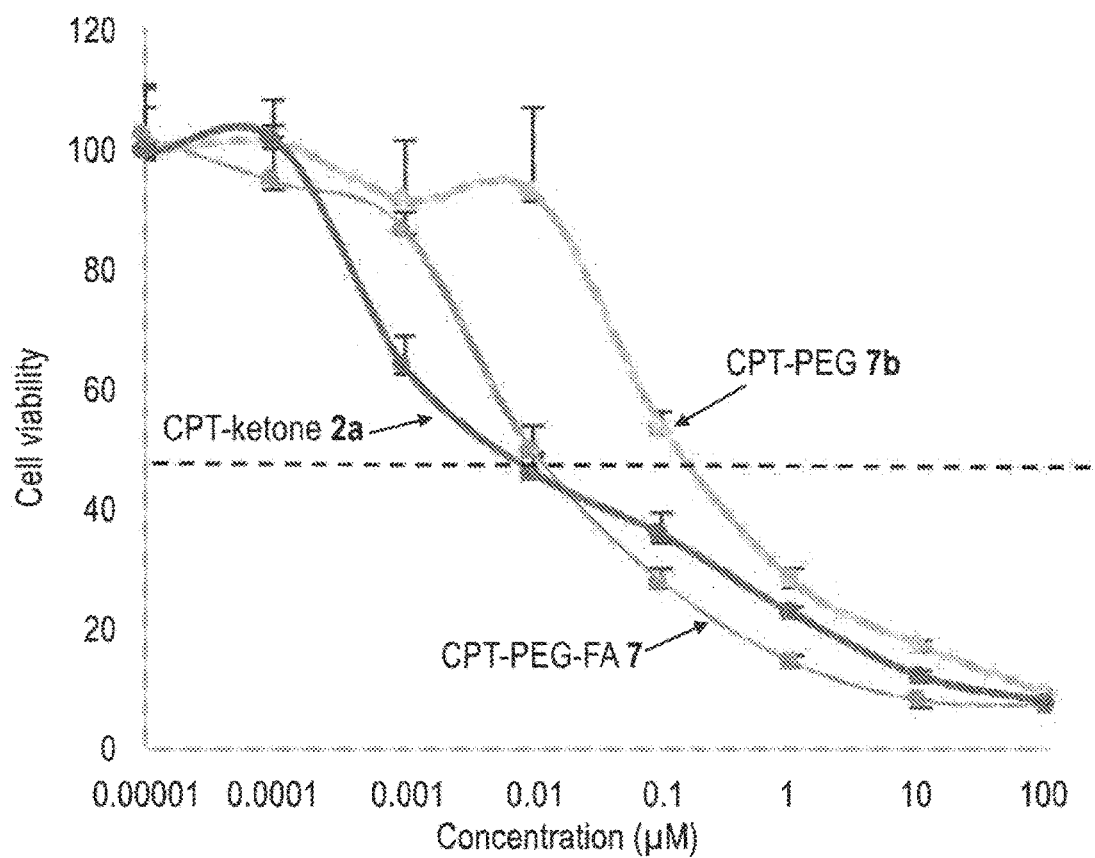

The binding affinity of folate-conjugate 7 with FR receptors was evaluated with highly expressed-FR KB cells (HiFR-KB). CPT-PEG derivative 7b, which lacks the folic acid was used as a control (FIG. 7A). The obtained measurements showed 82% binding of conjugate 7 to FR receptors in comparison to that of free folic acid. Cytotoxicity evaluation of CPT-folic acid conjugate 7 on HiFR KB cells results with relatively similar $IC_{50}$ values for CPT-ketone 2a and its folic acid conjugate 7 (FIG. 7B). CPT-PEG derivative 7b showed $IC_{50}$ value of 15-fold higher in comparison to that of conjugate 7. These results support the cell-penetrating ability of the folic acid-CPT conjugate and in vitro CPT-ketone controlled-release through the acid-labile semicarbazone linkage.

APPENDIX

Scheme 1. Employing of sodium ketal sulfinate 1 for tagging a heteroarene C-H inert bond with a ketone functional group and its bioconjugation through an acid-labile hydrazone linkage or a photo-labile ketal group for controlled-release applications

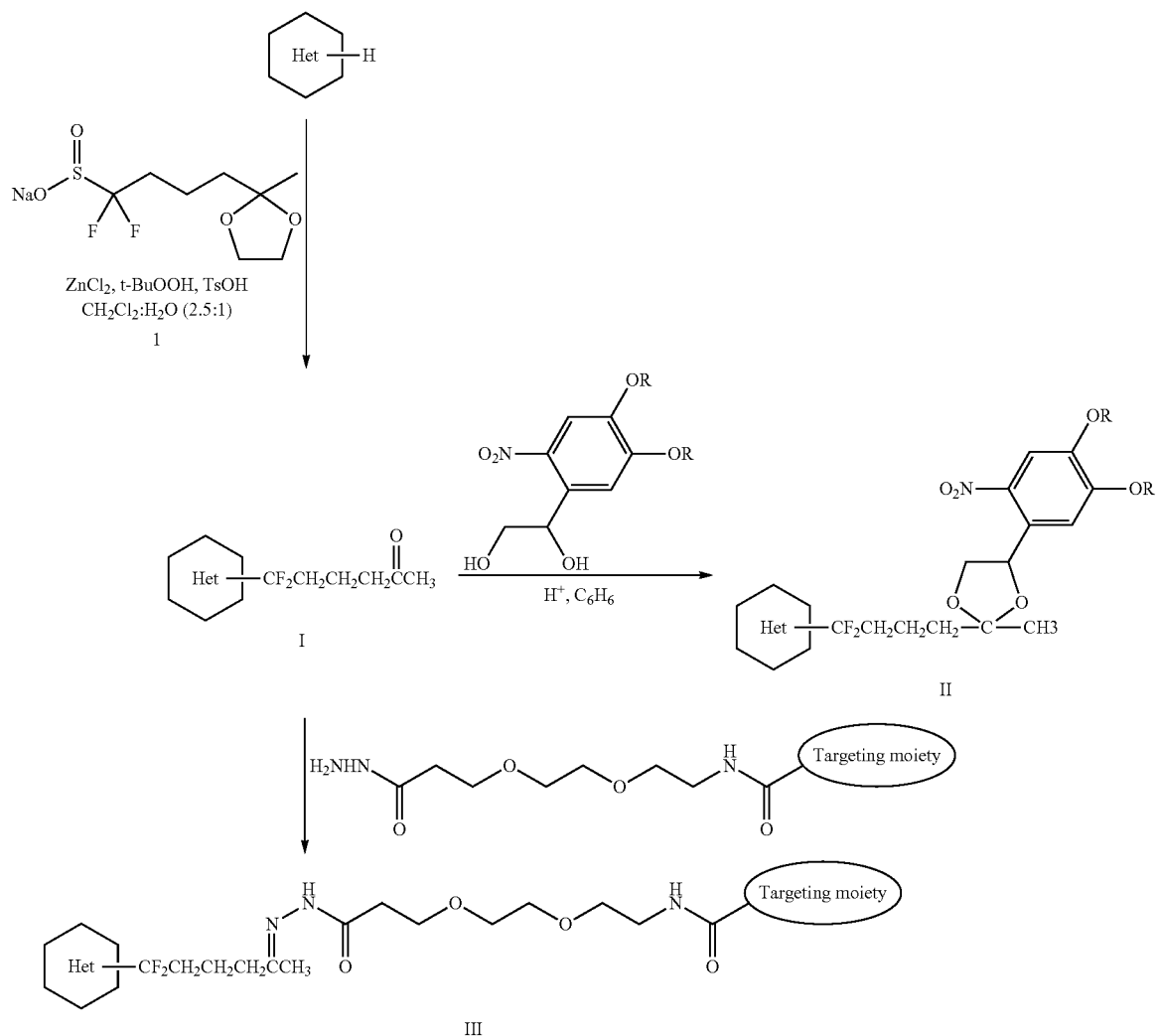

Scheme 2. Chemical synthesis of sodium ketal sulfinate 1
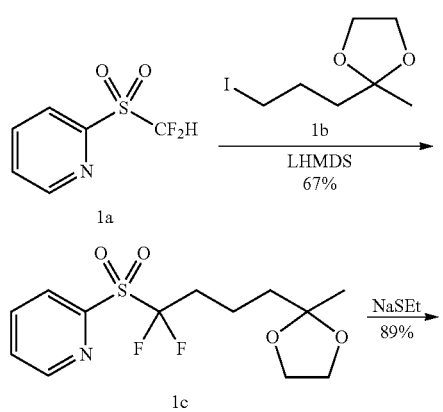
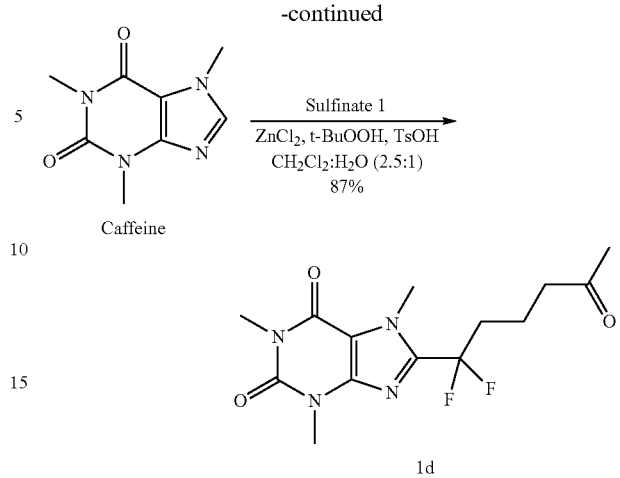
Scheme 3. Chemical synthesis of compound 10
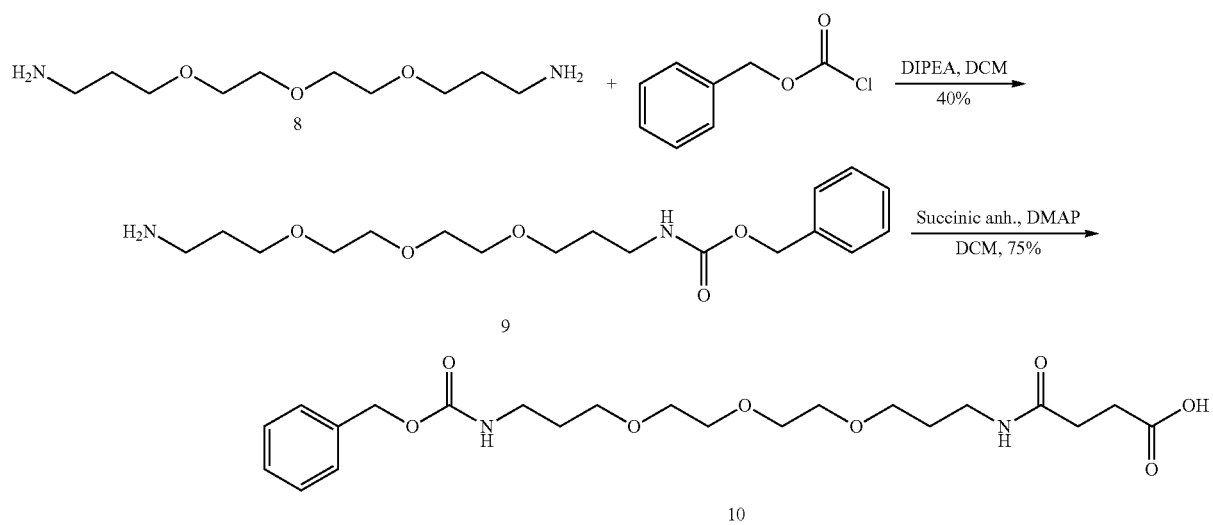
Scheme 4. Chemical synthesis of compound 13
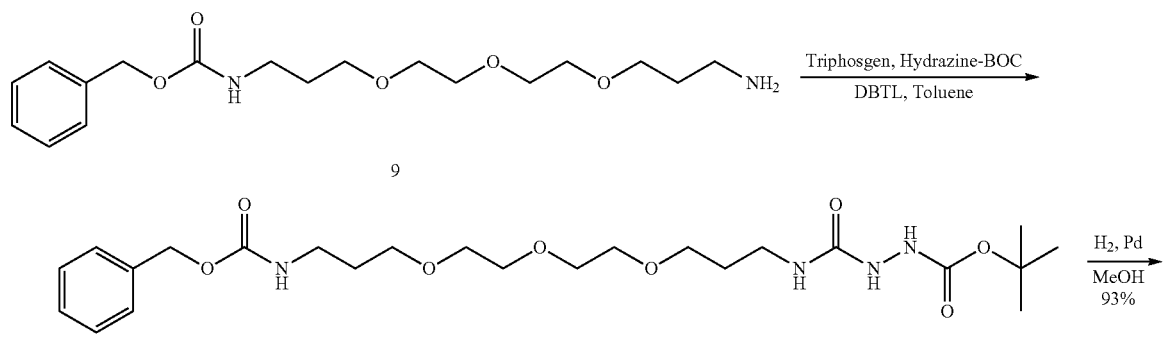

-continued
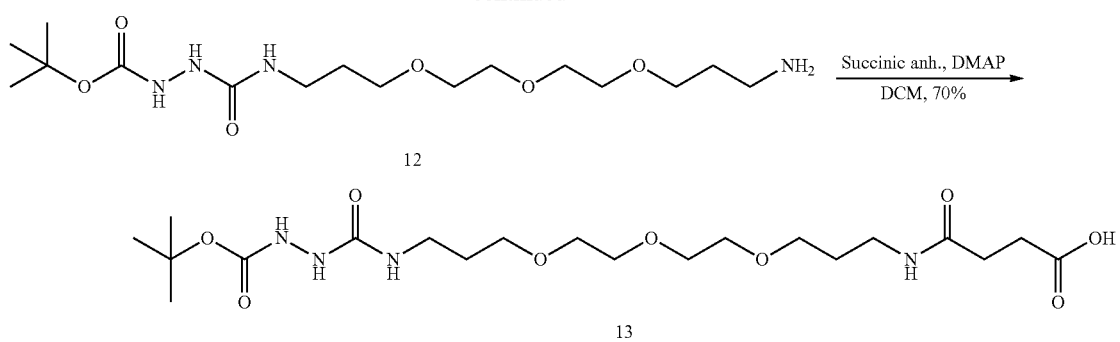
Scheme 5. Chemical synthesis of compound 15
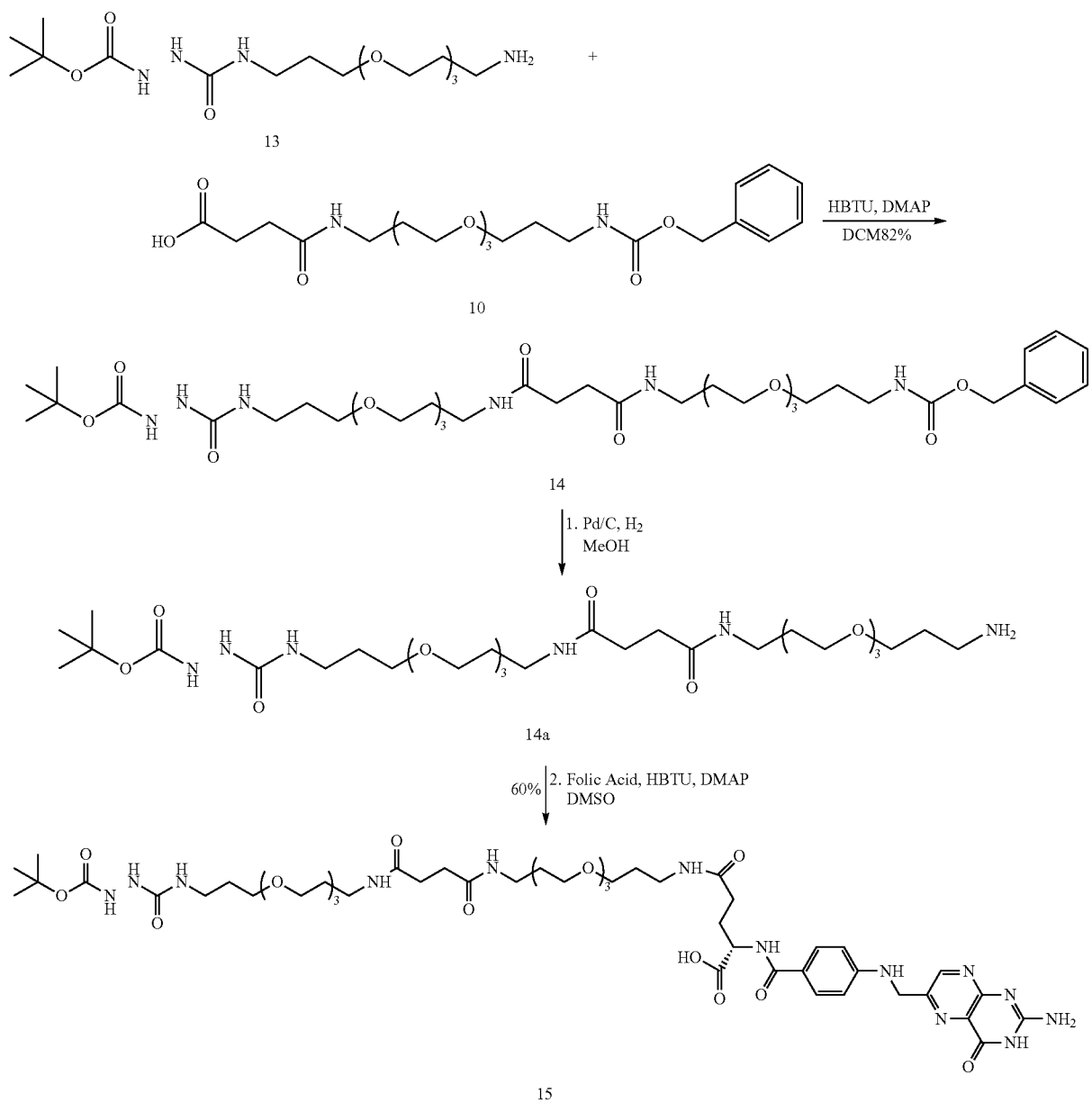

Scheme 6. Chemical synthesis of compound 7
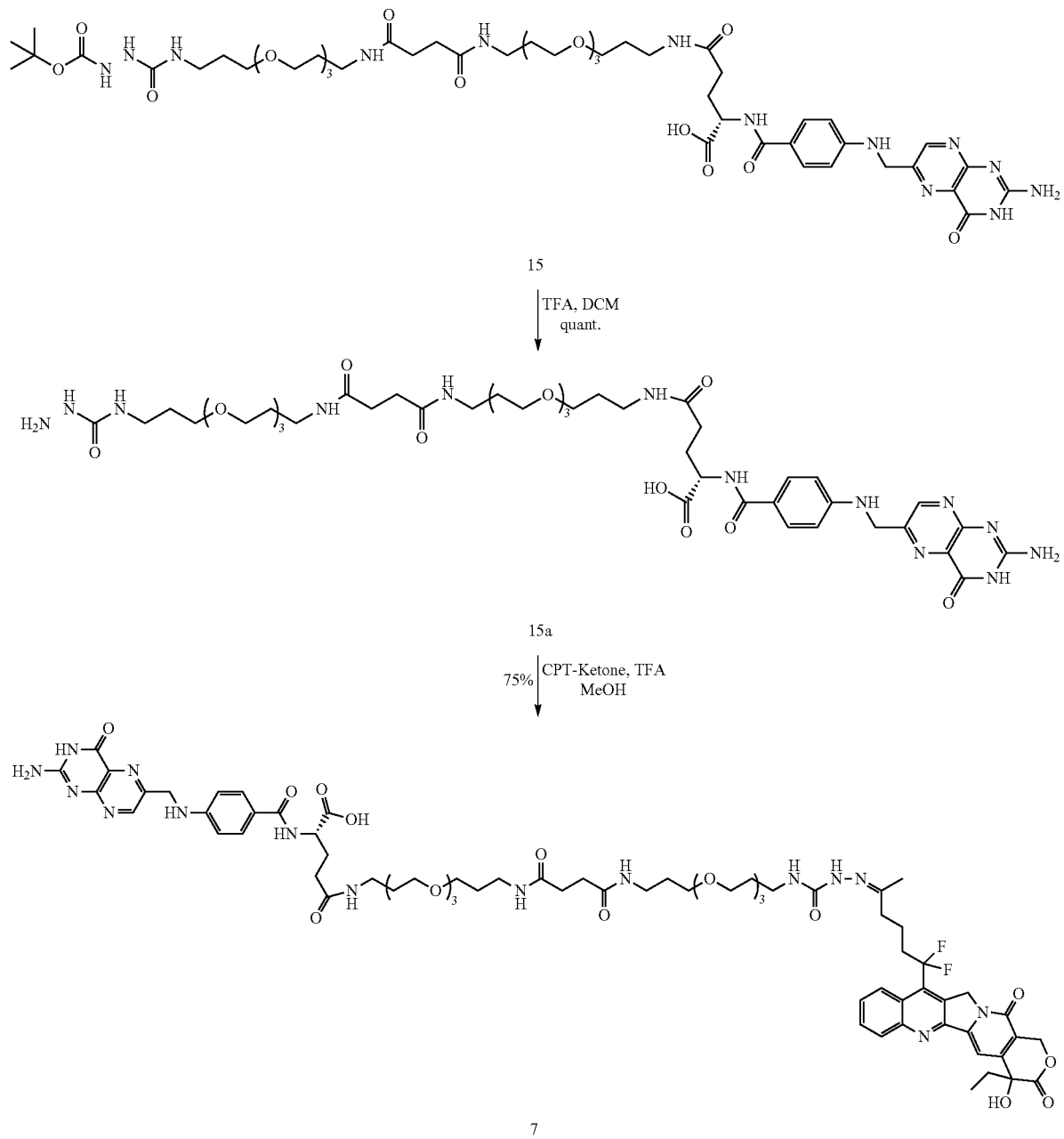
Scheme 7. Chemical synthesis of compound 7b
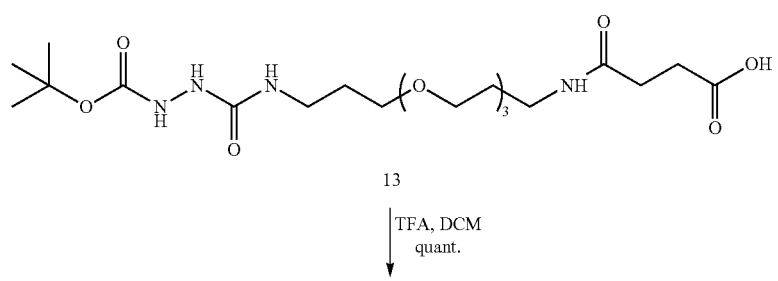

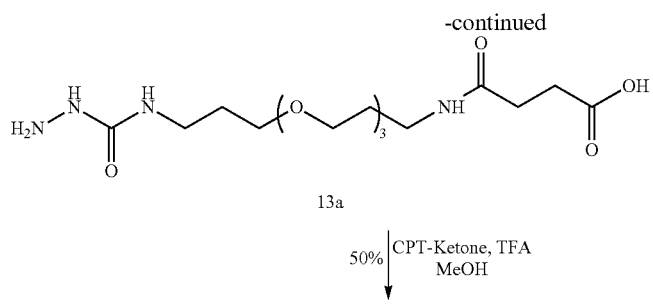
13a
50% | CPT-Ketone, TFA
        MeOH
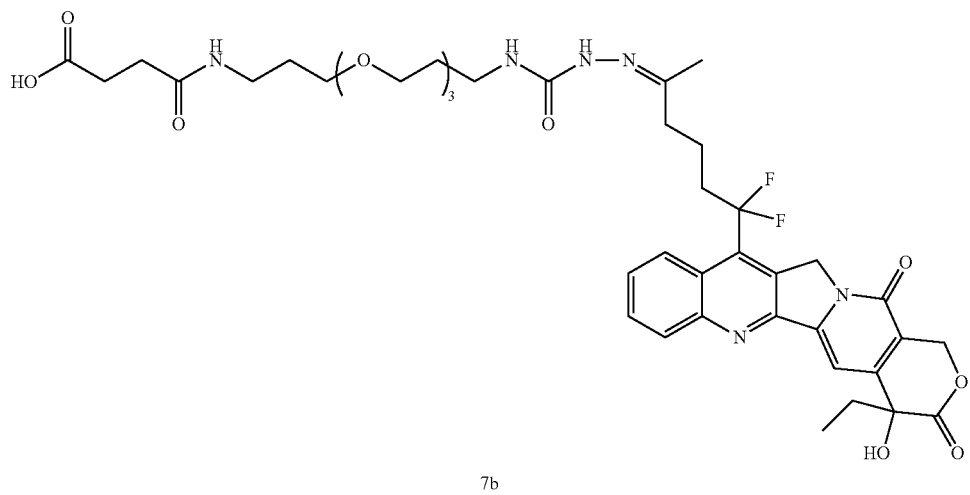
7b
Scheme 8. Chemical synthesis of compound 6
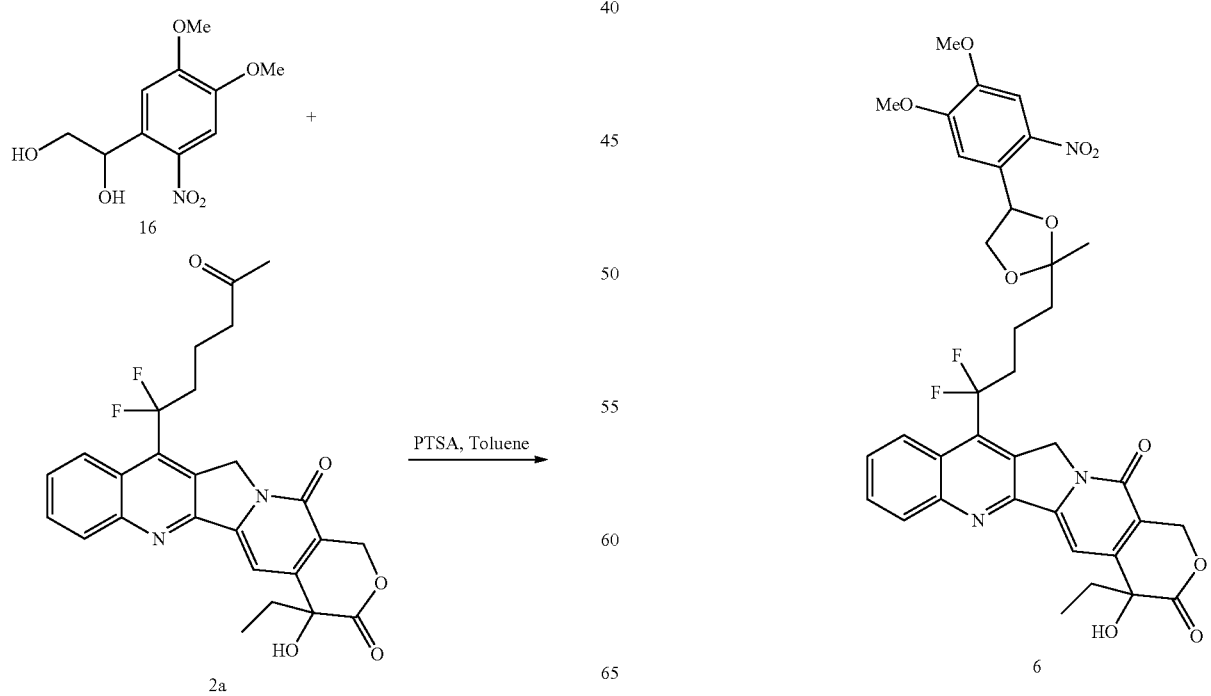

Scheme 9. Release of CPT-ketone 2a from a folic acid conjugate via acid-labile controlled-release mechanism of a semicarbazone linkage.

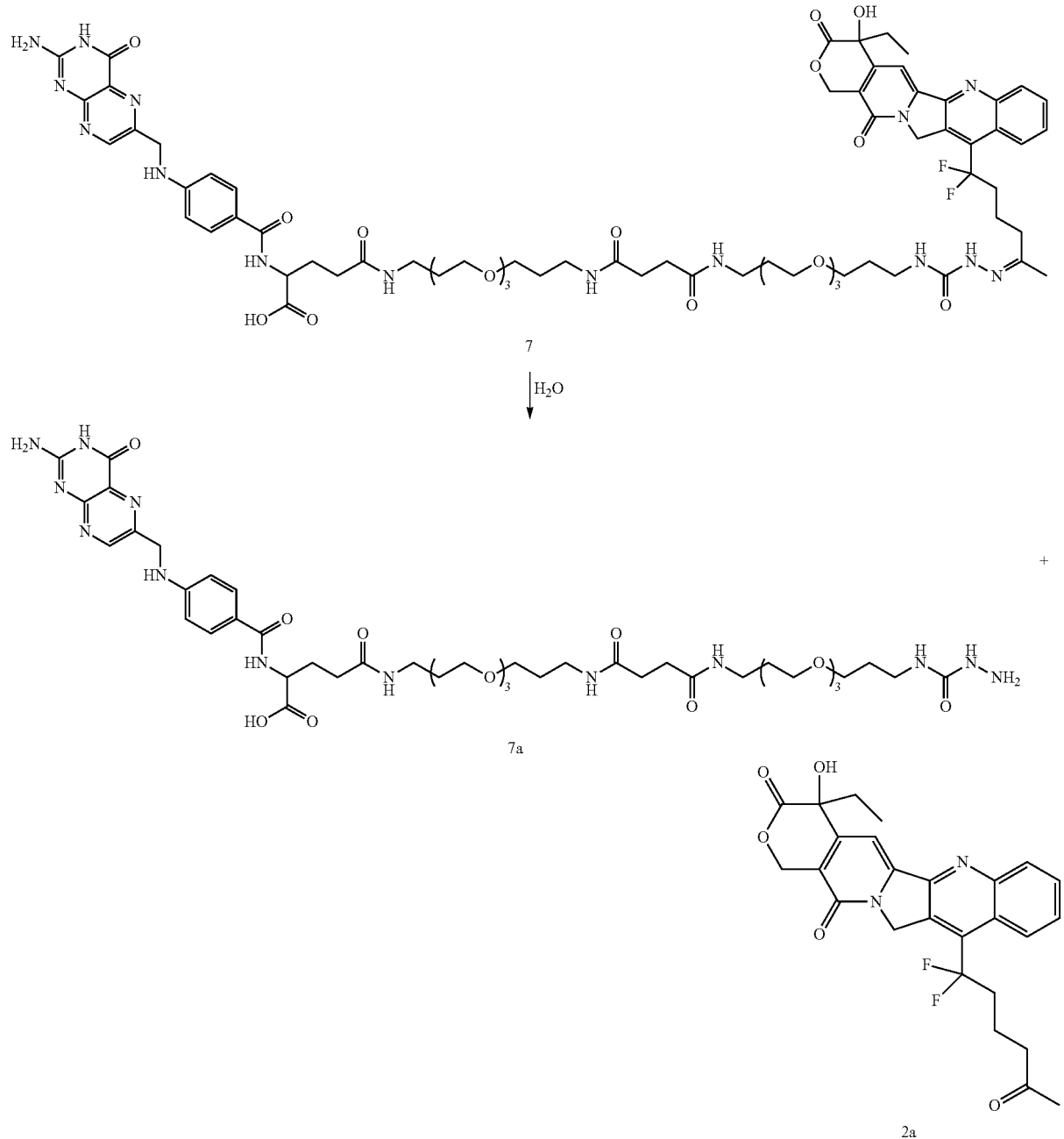

REFERENCES

Bruckl, T.; Baxter, R. D.; Ishihara. Y.; Baran, P. S.: Innate and guided C—H functionalization logic. *Acc Chem Res* 2012, 45, 826-839

Fujiwara, Y.; Dixon. J. A.; O'Hara, F.; Funder, E. D.; Dixon, D. D.; Rodriguez, R. A.; Baxter, R. D.; Herle, B.; Sach, N.; Collins, M, R.; Ishihara, Y.; Baran. P. S., Practical and innate carbon-hydrogen functionalization of heterocycles. *Nature* 2012, 492, 95-99

Gravel, D.; Hebert. J.; Thoraval. D.; *Can J Chem* 1983, 61, 400-410

Gui, J.; Zhou, Q.; Pan, C. M.; Yabe, Y.; Burns, A. C.; Collins, M, R.; Ornelas, M. A.; Ishihara. Y.; Baran, P. S., C—H methylation of heteroarenes inspired by radical SAM methyl transferase. *J. Am. Chem. Soc.* 2014, 136, 4853-4856

Ji, Y.; Brueckl. T.; Baxter, R. D.; Fujiwara. Y.; Seiple, I. B.; Su, S.; Blackmond, D. G.; Baran, P. S., Innate C—H trifluoromethylation of heterocycles. *Proc. Natl. Acad. Sci. U.S.A.* 2011, 108, 14411-14415

Klan. P.; Solomek, T.; Bochet. C. G.; Blane, A.; Givens, R.; Rubina. M.; Popik, V.; Kostikov, A.; Wirz, *J., Chem. Rev.* 2013, 113, 119-191

Kolb, H. C.; Finn, M. G.; Sharpless. K. B., Click chemistry: diverse chemical function from a few good reactions. *Angew. Chem. Int. Ed. Engl.* 2001, 40, 2004-2021

Lu, M.; Fedoryak, O. D.; Moister, B, R.; Dore, T. M., *Org. Lett.* 2003, 5, 2119-2122

Patil, R.; Portilla-Arias, J.; Ding, H.; Konda, B.; Rekechenetskiy. A.; Inoue, S.; Black, K. L.; Holler. E.; Ljubimova, J. Y., *International journal of molecular sciences* 2012, 13, 11681-11693

Ulrich, S.; Boturyn. D.; Marra, A.; Renaudet, O.; Dumy, P.: Oxime ligation: a chemoselective click-type reaction for accessing multifunctional biomolecular constructs. *Chemistry* 2014, 20, 34-41

Yang, J.; Chen. H.; Vlahov, I, R., Cheng. J. X.; Low. P. S., *J. Pharmacol. Exp. Ther.* 2007, 321, 462-468

Zhao, X.; Li, H.; Lee, R. J., *Expert opinion on drug delivery* 2008, 5, 309-319

Zhou, Q. Gui, J.; Pan. C. M.; Albone, E.; Cheng, X.; Suh, E. M.; Grasso. L.; Ishihara, Y.; Baran, P. S., Bioconjugation by native chemical tagging of C—H bonds. *J. Am. Chem. Soc.* 2013a, 135, 12994-12997

Zhou. Q.; Ruffoni, A.; Gianatassio, R.; Fujiwara, Y.; Sella. E.; Shabat, D.; Baran, P. S., Direct synthesis of fluorinated heteroarylether bioisosteres. *Angew. Chem. Int. Ed. Engl.* 2013b, 52, 3949-3952

What is claimed is:

1. A compound of the formula I:

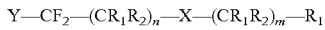

wherein

Y is a drug or a bioactive reagent, comprising a heteroaromatic ring and linked via a carbon atom of said heteroaromatic ring;

X is carbonyl, or cyclic ketal substituted with 1 to 4 groups each independently is phenyl or naphtyl substituted ortho to the carbon of attachment with —$NO_2$, and optionally further substituted at any position other than ortho to the carbon of attachment with one or more groups each independently selected from the group consisting of —O—($C_1$-$C_8$), —($C_1$-$C_8$)alkyl, —N(R')$_2$, and halogen, wherein R' each independently is —($C_1$-$C_8$)alkyl or H;

$R_1$ and $R_2$ each independently is H, halogen, —$OR_3$, —CO—$R_3$, —CO—$OR_3$, —OCO—$OR_3$, —OCO—N($R_3$)$_2$, —CN, —$NO_2$, —$SR_3$, —N($R_3$)$_2$, —CO—N($R_3$)$_2$, —($C_1$-$C_8$)alkyl, —($C_2$-$C_8$)alkenyl, —($C_2$-$C_8$)alkynyl, ($C_3$-$C_{10}$)cycloalkyl, ($C_6$-$C_{14}$)aryl, or 4-12-membered heterocyclyl;

$R_3$ is H, —($C_1$-$C_{18}$)alkyl, —($C_2$-$C_{18}$)alkenyl, or —($C_2$-$C_{18}$)alkynyl; and n and m each independently is an integer of 1-8, or a pharmaceutically acceptable salt thereof.

2. The compound of claim 1, wherein:
(i) $R_1$ and $R_2$ each independently is H, halogen, —$OR_3$, —CO—$R_3$, —CO—$OR_3$, —OCO—$OR_3$, —OCO—N($R_3$)$_2$, —CN, —$NO_2$, —$SR_3$, —N($R_3$)$_2$, —CO—N($R_3$)$_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl, wherein $R_3$ is H, methyl, ethyl or propyl;
(ii) n is 3, 4, or 5; or
(iii) m is 1, 2, or 3.

3. The compound of claim 1, wherein $R_1$ and $R_2$ each independently is H, halogen, —$OR_3$, —CO—$R_3$, —CO—$OR_3$, —OCO—$OR_3$, —OCO—N($R_3$)$_2$, —CN, —$NO_2$, —$SR_3$, —N($R_3$)$_2$, —CO—N($R_3$)$_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl, wherein $R_3$ is H, methyl, ethyl or propyl; n is 3, 4, or 5; and m is 1, 2, or 3.

4. The compound of claim 3, wherein $R_1$ and $R_2$ are H.

5. The compound of claim 1, wherein Y is an anticancer drug, antineoplastic drug, antifungal drug, antibacterial drug, antiviral drug, cardiac drug, neurological drug, psychoactive drug, alkaloid, antibiotic, bioactive peptide, steroid, steroid hormone, peptide hormone, interferon, interleukin, narcotic, nucleic acid, pesticide, or prostaglandin.

6. The compound of claim 5, wherein said anticancer drug is a chemotherapeutic drug; or said antineoplastic drug is an alkylating antineoplastic agent.

7. The compound of claim 1, wherein X is (i) carbonyl; or (ii) cyclic ketal substituted with 1 or 2 phenyl groups each independently substituted ortho to the carbon of attachment with —$NO_2$, and optionally further substituted at any position other than ortho to the carbon of attachment with one or more groups each independently is —O—($C_1$-$C_8$).

8. The compound of claim 7, wherein X is cyclic ketal substituted with 4,5-dimethoxy,2-nitrophenyl group.

9. A conjugate of the formula II:

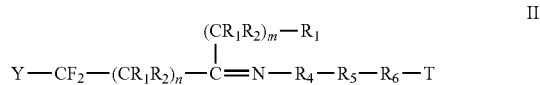

Y is a drug or a bioactive reagent, comprising a heteroaromatic ring and linked via a carbon atom of said heteroarimatic ring;

$R_1$ and $R_2$ each independently is H, halogen, —$OR_3$, —CO—$R_3$, —CO—$OR_3$, —OCO—$OR_3$, —OCO—N($R_3$)$_2$, —CN, —$NO_2$, —$SR_3$, —N($R_3$)$_2$, —CO—N($R_3$)$_2$, —($C_1$-$C_8$)alkyl, —($C_2$-$C_8$)alkenyl, —($C_2$-$C_8$)alkynyl, ($C_3$-$C_{10}$)cycloalkyl, ($C_6$-$C_{14}$)aryl, or 4-12-membered heterocyclyl;

$R_3$ is H, —($C_1$-$C_{18}$)alkyl, —($C_2$-$C_{18}$)alkenyl, or —($C_2$-$C_{18}$)alkynyl;

$R_4$ is absent, or is selected from the group consisting of —NH—($CH_2$)$_p$—, —NH—CO—($CH_2$)$_p$—, —NH—CO—NH—($CH_2$)$_p$—, —NH—CO—O—($CH_2$)$_p$—, —O—($CH_2$)$_p$—, —O—CO—($CH_2$)$_p$—, —O—CO—NH—($CH_2$)$_p$—, and —O—CO—O—($CH_2$)$_p$—;

$R_5$ is a polymer-, protein-, peptide-, or carbohydrate moiety;

$R_6$ is H, —($CH_2$)$_y$—OH, —($CH_2$)$_y$—SH, —($CH_2$)$_y$—$NH_2$, —($CH_2$)$_y$—COOH, —($CH_2$)$_y$—$SO_3$H, or a divalent radical selected from the group consisting of —($CH_2$)$_y$—O—, —($CH_2$)$_y$—S—, —($CH_2$)$_y$—NH—, —($CH_2$)$_y$—OCO— and —($CH_2$)$_y$—$SO_3$—;

n and m each independently is an integer of 1-8;

p and y each independently is an integer of 0-8; and

T is absent, or is a targeting moiety capable of binding to an extracellular antigen and linked via a functional group thereof, provided that when T is absent $R_6$ is not a divalent radical, and when T is a targeting moiety $R_6$ is a divalent radical, or a pharmaceutically acceptable salt thereof.

10. The conjugate of claim 9, wherein:
(i) $R_1$ and $R_2$ each independently is H, halogen, —$OR_3$, —CO—$R_3$, —CO—$OR_3$, —OCO—$OR_3$, —OCO—N($R_3$)$_2$, —CN, —$NO_2$, —$SR_3$, —N($R_3$)$_2$, —CO—N($R_3$)$_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$)aryl, or 4-12-membered heterocyclyl, wherein $R_3$ is H, methyl, ethyl or propyl;

(ii) n is 3, 4, or 5;
(iii) m is 1, 2, or 3;
(iv) $R_4$ is —NH—CO—$(CH_2)_p$— or —NH—CO—NH—$(CH_2)_p$—;
(v) $R_5$ is a polymer moiety, and said polymer is linear or branched polyethylene glycol (PEG) or copolymers thereof; a pseudo PEG interrupted by at least one group each independently selected from the group consisting of —NH—CO—, —CO—NH—, and ($C_3$-$C_8$)alkylene interrupted by at least two groups each independently selected from the group consisting of —NH—CO— and —CO—NH—; poly(lactic acid) or copolymers thereof; polyesters selected from the group consisting of polylactide (PLA), polyglycolide (PGA), polycaprolactone (PCL) and copolymers thereof; or polyamides based on polymethacrylamide or copolymers thereof;
(vi) $R_5$ is a protein moiety, and said protein is albumin, a modified albumin, or a protein containing globin-like domains having long half-life in circulation;
(vii) $R_5$ is a peptide moiety;
(viii) $R_5$ is a carbohydrate moiety;
(ix) Y is an anticancer drug, antineoplastic drug, antifungal drug, antibacterial drug, antiviral drug, cardiac drug, neurological drug, psychoactive drug, alkaloid, antibiotic, bioactive peptide, steroid, steroid hormone, peptide hormone, interferon, interleukin, narcotic, nucleic acid, pesticide, or prostaglandin; or
(x) said targeting moiety is a protein, peptide, polypeptide, glycoprotein, lipoprotein, lipid, phospholipid, oligonucleotide or a mimic thereof, steroid, hormone, lymphokine, growth factor, albumin, cytokine, enzyme, coenzyme, vitamin, cofactor, human antigen, hapten, receptor protein, antibody or a fragment thereof, a substance used or modified such that it functions as a targeting moiety, or a combination thereof, preferably a vitamin such as vitamin B9 (folic acid).

11. The conjugate of claim 10, wherein said polymer is linear or branched PEG; or a pseudo PEG having the structure (—$CH_2$—$CH_2$—$O$)$_3$—$(CH_2)_3$—NH—CO—$(CH_2)_2$—CO—NH—$(CH_2)_3$—$(O$—$CH_2$—$CH_2$-$)_3$.

12. The conjugate of claim 10, wherein said anticancer drug is a chemotherapeutic drug; or said antineoplastic drug is an alkylating antineoplastic agent.

13. The conjugate of claim 9 wherein $R_1$ and $R_2$ each independently is H, halogen, —$OR_3$, —CO—$R_3$, —CO—$OR_3$, —OCO—$OR_3$, —OCO—$N(R_3)_2$, —CN, —$NO_2$, —$SR_3$, —$N(R_3)_2$, —CO—$N(R_3)_2$, —($C_1$-$C_4$)alkyl, —($C_2$-$C_4$)alkenyl, —($C_2$-$C_4$)alkynyl, ($C_3$-$C_{10}$)cycloalkyl, ($C_6$-$C_{14}$) aryl, or 4-12-membered heterocyclyl, wherein $R_3$ is H, methyl, ethyl or propyl; n is 3, 4, or 5; m is 1, 2, or 3; $R_4$ is —NH—CO—$(CH_2)_p$— or —NH—CO—NH—$(CH_2)_p$—; and $R_5$ is a PEG moiety or a pseudo PEG moiety interrupted by at least one group each independently selected from the group consisting of —NH—CO—, —CO—NH—, and ($C_3$-$C_8$)alkylene interrupted by at least two groups each independently selected from the group consisting of —NH—CO— and —CO—NH—.

14. The conjugate of claim 13, wherein $R_1$ and $R_2$ are H; n is 3; m is 1; and $R_5$ is a PEG moiety or a pseudo PEG moiety having the structure (—$CH_2$—$CH_2$—$O$)$_3$—$(CH_2)_3$—NH—CO—$(CH_2)_2$—CO—NH—$(CH_2)_3$—$(O$—$CH_2$—$CH_2$-$)_3$.

15. The conjugate of claim 14, wherein (i) $R_6$ is a divalent radical; or (ii) $R_6$ is H, —$(CH_2)_y$—OH, —$(CH_2)_y$—SH, —$(CH_2)_y$—$NH_2$, —$(CH_2)_y$—COOH or —$(CH_2)_y$—$SO_3H$, preferably —$(CH_2)_y$—SH, —$(CH_2)_y$—$NH_2$, or —$(CH_2)_y$—COOH; and T is absent.

16. The conjugate of claim 15, wherein $R_6$ is —$(CH_2)_y$—NH— and said targeting moiety is folic acid linked via a carboxylic group thereof.

17. The conjugate of claim 16, wherein (i) $R_4$ is —NH—CO—NH—$CH_2$—; $R_5$ is a pseudo PEG moiety having the structure (—$CH_2$—$CH_2$—$O$)$_3$—$(CH_2)_3$—NH—CO—$(CH_2)_2$—CO—NH—$(CH_2)_3$—$(O$—$CH_2$—$CH_2$-$)_3$; $R_6$ is —$(CH_2)$—NH—; and Y is camptothecin, 10-hydroxycamptothecin, temozolomide, bosutinib, or methotrexate; (ii) $R_4$ is —NH—CO—$CH_2$—; $R_5$ is a pseudo PEG moiety having the structure (—$CH_2$—$CH_2$—$O$)$_3$—$(CH_2)_3$—NH—CO—$(CH_2)_2$—CO—NH—$(CH_2)_3$—$(O$—$CH_2$—$CH_2$-$)_3$; $R_6$ is —$(CH_2)$—NH—; and Y is camptothecin, 10-hydroxycamptothecin, temozolomide, bosutinib, or methotrexate; or (iii) $R_4$ is —NH—CO—; $R_5$ is a PEG moiety having the structure (—$CH_2$—$CH_2$—$O$)$_3$—; $R_6$ is —$(CH_2)_2$—NH—; and Y is camptothecin, 10-hydroxycamptothecin, temozolomide, bosutinib, or methotrexate.

18. The conjugate of claim 15, wherein y is 1, 2 or 3.

19. A pharmaceutical composition comprising a compound of claim 1 wherein X is not carbonyl, or a pharmaceutically acceptable salt thereof, and a pharmaceutically acceptable carrier.

20. A method for treatment of a cancer characterized by folate receptor overexpressing cells in an individual in need thereof, said method comprising administering to said individual a therapeutically effective amount of a conjugate of claim 9 or a pharmaceutically acceptable salt thereof, wherein Y is an anticancer drug or an antineoplastic drug, and said targeting moiety is folic acid linked via a carboxylic group thereof.

21. The method of claim 20, wherein said anticancer drug is a chemotherapeutic drug; said antineoplastic drug is an alkylating antineoplastic agent; or said folic acid is linked via its gamma-carboxyl group.

22. A pharmaceutical composition comprising a conjugate of claim 9 or a pharmaceutically acceptable salt thereof, and a pharmaceutically acceptable carrier.

23. The compound of claim 6, wherein said chemotherapeutic drug is camptothecin or a derivative thereof, bosutinib, or methotrexate; or said alkylating antineoplastic agent is temozolomide, uramustine, or bendamustine.

24. The conjugate of claim 12, wherein said chemotherapeutic drug is camptothecin or a derivative thereof, bosutinib, or methotrexate; or said alkylating antineoplastic agent is temozolomide, uramustine, or bendamustine.

25. The method of claim 20, wherein said cancer is carcinoma.

* * * * *

UNITED STATES PATENT AND TRADEMARK OFFICE
CERTIFICATE OF CORRECTION

PATENT NO. : 10,420,845 B2
APPLICATION NO. : 15/737247
DATED : September 24, 2019
INVENTOR(S) : Doron Shabat It is certified that error appears in the above-identified patent and that said Letters Patent is hereby corrected as shown below:

On the Title Page

In Column 2, other publications, Line 4, delete "1101" and insert -- 101 --.

In the Specification

In Column 1, Line 40, delete "tetrahidrofuran" and insert -- tetrahydrofuran --.

In Column 2, Line 28, delete "naphtyl" and insert -- naphthyl --.

In Column 2, Line 46, delete "formula H" and insert -- formula II --.

In Column 2, Lines 56-57, delete "heteroarimatic" and insert -- heteroaromatic --.

In Column 3, Line 44, delete "formula IT" and insert -- formula II --.

In Column 4, Line 29, delete "most." and insert -- most, --.

In Column 4, Line 52, delete "pseudoPEG" and insert -- psedo PEG --.

In Column 5, Line 6, delete "naphtyl" and insert -- naphthyl --.

In Column 5, Line 15, delete "N(R_)2" and insert -- N(R$_3$)$_2$ --.

In Column 5, Line 44, delete "like," and insert -- like. --.

In Column 8, Lines 35-36, delete "heteroarimatic" and insert -- heteroaromatic --.

In Column 8, Line 55, delete "—(CH2)—NH—" and insert -- "—(CH2)Y—NH— --.

Signed and Sealed this
Third Day of November, 2020

Andrei Iancu
*Director of the United States Patent and Trademark Office*

CERTIFICATE OF CORRECTION (continued)
U.S. Pat. No. 10,420,845 B2

In Column 8, Line 57, delete "1-8:" and insert -- 1-8; --.

In Column 9, Line 3, delete "(C3-C10))" and insert -- (C3-C10) --.

In Column 10, Line 35, delete "aminobutiric acid" and insert -- aminobutyric acid --.

In Column 10, Line 63, delete "oligosaccarides" and insert -- oligosaccharides --.

In Column 11, Line 2, delete "Syalyl Lewis X" and insert -- Syalyi Lewis X --.

In Column 11, Line 28, delete "formula H" and insert -- formula II --.

In Column 12, Line 62, delete "formula I" and insert -- formula II --.

In Column 13, Line 32, delete "in-hexyl" and insert -- n-hexyl --.

In Column 14, Lines 11-12, delete "Eu-fectins" and insert -- Eu-functions --.

In Column 16, Line 48, delete "cells." and insert -- cells, --.

In Column 17, Line 43, delete "equiv" and insert -- equiv. --.

In Column 17, Line 67, delete "Kulfinate" and insert -- Sulfinate --.

In Column 18, Line 9, delete "MHz." and insert -- MHz, --.

In Column 19, Line 17, delete "mL" and insert -- mL, --.

In Column 19, Lines 55-56, delete "(10mL)." and insert -- (10mL), --.

In Column 22, Line 15, delete "IL" and insert -- 1L --.

In Column 24, Line 4, delete "(I)." and insert -- (II). --.

In Column 24, Line 8, delete "sulphone" and insert -- sulfone --.

In the Claims

In Column 39, Line 35, Claim 1, delete "naphtyl" and insert -- naphthyl --.

In Column 40, Lines 30-31, Claim 9, delete "heteroarimatic" and insert -- heteroaromatic --.